(12) United States Patent
Wisniewski et al.

(10) Patent No.: US 11,332,506 B2
(45) Date of Patent: *May 17, 2022

(54) IMMUNOTHERAPEUTIC MODULATION OF AMYLOIDOGENIC DISEASE USING NON-FIBRILLOGENIC, NON-AMYLOIDOGENIC POLYMERIZED PROTEINS AND PEPTIDES

(71) Applicant: New York University, New York, NY (US)

(72) Inventors: Thomas M. Wisniewski, Staten Island, NY (US); Fernando Goni, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 15/933,146

(22) Filed: Mar. 22, 2018

(65) Prior Publication Data

US 2019/0338004 A1   Nov. 7, 2019

Related U.S. Application Data

(63) Continuation of application No. 13/550,316, filed on Jul. 16, 2012, now Pat. No. 9,926,353.

(60) Provisional application No. 61/509,442, filed on Jul. 19, 2011, provisional application No. 61/509,320, filed on Jul. 19, 2011.

(51) Int. Cl.
| | |
|---|---|
| *C07K 14/47* | (2006.01) |
| *A61K 39/00* | (2006.01) |
| *G01N 33/68* | (2006.01) |
| *A61K 9/00* | (2006.01) |
| *C07K 16/18* | (2006.01) |

(52) U.S. Cl.
CPC ........ *C07K 14/4711* (2013.01); *A61K 9/0056* (2013.01); *A61K 39/0007* (2013.01); *C07K 16/18* (2013.01); *G01N 33/6896* (2013.01); *A61K 2039/523* (2013.01); *A61K 2039/64* (2013.01); *C07K 2317/20* (2013.01); *G01N 2333/4709* (2013.01); *G01N 2800/28* (2013.01); *G01N 2800/2821* (2013.01)

(58) Field of Classification Search
CPC ............ C07K 14/4711; A61K 39/0007; A61K 2039/64; G01N 33/6896; G01N 2333/4709; G01N 2800/28; G01N 2800/2821

See application file for complete search history.

(56) References Cited

U.S. PATENT DOCUMENTS

| | | |
|---|---|---|
| 4,180,562 A | 12/1979 | Patterson et al. |
| 5,080,896 A | 1/1992 | Visser et al. |
| 5,434,170 A | 7/1995 | Andrulis, Jr. |
| 5,688,651 A | 11/1997 | Solomon |
| 5,695,766 A | 12/1997 | Paul et al. |
| 5,843,446 A | 12/1998 | Ladd et al. |
| 5,948,763 A | 9/1999 | Soto-Jara et al. |
| 6,022,859 A | 2/2000 | Kiessling et al. |
| 6,274,615 B1 | 8/2001 | Pappolla et al. |
| 6,462,171 B1 | 10/2002 | Soto-Jara et al. |
| 6,670,195 B1 | 12/2003 | Ghiso et al. |
| 6,713,450 B2 | 3/2004 | Frangione et al. |
| 6,866,849 B2 | 3/2005 | Schenk |
| 6,962,707 B2 | 11/2005 | Schenk |
| 7,427,655 B2 | 9/2008 | Frangione et al. |
| 7,479,482 B2 | 1/2009 | Frangione et al. |
| 7,632,816 B2 | 12/2009 | Wisniewski et al. |
| 7,700,107 B2 | 4/2010 | Frangione et al. |
| 7,902,328 B2 | 3/2011 | Hillen et al. |
| 8,906,382 B2 | 12/2014 | Wisniewski et al. |
| 2002/0009445 A1 | 1/2002 | Du et al. |
| 2002/0037290 A1 | 3/2002 | Armen |
| 2002/0077288 A1 | 6/2002 | Frangione et al. |
| 2003/0166558 A1 | 9/2003 | Frangione et al. |
| 2003/0219853 A1 | 11/2003 | Chou |
| 2004/0043935 A1 | 3/2004 | Frangione et al. |
| 2004/0214774 A1 | 10/2004 | Wisniewski et al. |
| 2005/0019330 A1 | 1/2005 | Schenk |
| 2006/0199771 A1 | 9/2006 | Chalifour et al. |
| 2007/0010435 A1 | 1/2007 | Frangione et al. |
| 2007/0059807 A1 | 3/2007 | Wisniewski et al. |
| 2007/0098721 A1 | 5/2007 | Hillen |
| 2007/0122421 A1 | 5/2007 | Medzhitov |
| 2008/0050383 A1 | 2/2008 | Sigurdsson et al. |

(Continued)

FOREIGN PATENT DOCUMENTS

| | | |
|---|---|---|
| EP | 0908727 A1 | 4/1999 |
| WO | WO 93/23432 A1 | 11/1993 |

(Continued)

OTHER PUBLICATIONS

Payne JW. Polymerization of proteins with glutaraldehyde. Biochem. J. 135, 867-873. (Year: 1973).*

Ilitchev AI et al. Hetero-oligomeric amyloid assembly and mechanism: Prion fragment PrP(106-126) catalyzes the islet amyloid polypeptide beta-hairpin. J. Am. Chem. Soc. 2018, 140, 9685-9695. (Year: 2018).*

Iljina M et al. Quantifying co-oligomer formation by alpha-synuclein. ACS Nano, 2018, 12, 10855-10866. (Year: 2018).*

Jensen PH et al. Binding of Abeta to alpha- and beta-synucleins: identification of segments in alpha-synuclein/NAC precursor that bind Abeta and NAC. Biochem. J. 1997, 323, 539-546. (Year: 1997).*

(Continued)

*Primary Examiner* — Kimberly Ballard
(74) *Attorney, Agent, or Firm* — Troutman Pepper Hamilton Sanders LLP (Rochester)

(57) ABSTRACT

The present invention is directed to polymerized products and compositions useful for the treatment and prevention of amyloid disease in a subject. The invention further relates to isolated antibodies that recognize a common conformational epitope of amyloidogenic proteins or peptides that are useful for the diagnosis, treatment, and prevention of amyloid disease.

23 Claims, 15 Drawing Sheets

Specification includes a Sequence Listing.

(56) References Cited

U.S. PATENT DOCUMENTS

| | | | |
|---|---|---|---|
| 2009/0081204 | A1 | 3/2009 | Frangione et al. |
| 2009/0163420 | A1 | 6/2009 | Frangione et al. |
| 2009/0175853 | A1 | 7/2009 | Frangione et al. |
| 2010/0284909 | A1 | 11/2010 | Wisniewski et al. |
| 2010/0298202 | A1 | 11/2010 | Jansen-West et al. |
| 2011/0117100 | A1 | 5/2011 | Markus et al. |
| 2013/0022544 | A1 | 1/2013 | Wisniewski et al. |
| 2013/0045216 | A1 | 2/2013 | Frangione et al. |

FOREIGN PATENT DOCUMENTS

| | | |
|---|---|---|
| WO | WO 94/17197 A1 | 8/1994 |
| WO | WO 95/31996 A1 | 11/1995 |
| WO | WO 96/39834 A1 | 12/1996 |
| WO | WO 98/15179 A1 | 4/1998 |
| WO | WO 98/39653 A1 | 9/1998 |
| WO | WO 99/27944 A1 | 6/1999 |
| WO | WO 99/27949 A1 | 6/1999 |
| WO | WO 99/48489 A2 | 9/1999 |
| WO | WO 00/71671 A2 | 11/2000 |
| WO | WO 00/72800 A2 | 12/2000 |
| WO | WO 00/72880 A2 | 12/2000 |
| WO | WO 2001090182 | 11/2001 |
| WO | WO 02/11669 A2 | 2/2002 |
| WO | WO 03/044051 A1 | 5/2003 |
| WO | WO 03/051374 A2 | 6/2003 |
| WO | WO2003045128 | 6/2003 |
| WO | WO2004056318 | 7/2004 |
| WO | WO2004087733 | 10/2004 |
| WO | WO2009009396 | 1/2009 |
| WO | WO2010016912 | 2/2010 |
| WO | WO2010129674 | 11/2010 |

OTHER PUBLICATIONS

Mandal PK et al. Interaction between Abeta peptide and a synuclein: Molecular mechanisms in overlapping pathology of Alzheimer's and Parkinson's in dementia with Lewy Body Disease. Neurochem. Res. 2006, 31, 1153-1162. (Year: 2006).*

Aguado et al., "Meeting Report—Novel adjuvants currently in clinical testing Nov. 2-4, 1998, Foundation Merieux, Annecy, France: A meeting sponsored by the World Health Organization." Vaccine (1999) 17:2321-2328.

Alberts et al., "Molecular Biology of the Cell", pp. 129-130 (1994).

Apostol MI, Towards a structural understanding of progression and transmission of prion diseases. Doctoral dissertation, University of California, Los Angeles, pp. 143-155 (2008).

Asuni et al., "Vaccination of Alzheimer's model mice with Abeta derivative in alum adjuvant reduces Abeta burden without microhemorrhages," Eur J Neurosci. (2006) vol. 24, No. 9, pp. 2530-2542.

Barghorn, S. et al., "Globular amyloid beta-peptide 1-42 oligomer—a homogenous and stable neuropathological protein in Alzheimer's disease", J. Neurochem 95:834-847 (2005).

Bendig 1995 "Humanization of rodent monoclonal antibodies by CDR grafting" Methods: a companion to methods in enzymology 8:83-93.

Benkirane 1993. "Antigenicity and immunogenicity of modified synthetic peptides containing D-amino acid residues. Antibodies to a D-enantiomer do recognize the parent L-hexapeptide and reciprocally," Journal of Biological Chemistry 268:26279-26285.

Biere et al., "Parkinson's disease-associated alpha-synuclein is more fibrillogenic than beta- and gamma-synuclein and cannot cross-seed its homologs," J. Biol Chem (2000) 275:34574-34579.

Bodles 2001. "Identification of the region of non-Ab component of Alzheimer's disease amyloid responsible for its aggregation and toxicity," Journal of Neurochemistry 78:384-395.

Boutajangout et al., "Diminished amyloid-beta burden in Tg2576 mice following a prophylactic oral immunization with a salmonella-based amyloid-beta derivative vaccine," J Alzheimers Dis. (2009) vol. 18, No. 4, pp. 961-972.

Bueler et al,. "Mice Devoid of PrP are Resistant to Scrapie," Cell (1993) 73:1339-1347.

Bueler et al., "Normal development and behavior of mice lacking the neuronal cell-surface PrP protein," Nature (1992) 356:577-582.

Buschle et al., "Transloading of tumor antigen-derived peptides into antigen-presenting cells," Proc. Natl. Sci. USA (1997) 94:3256-3261.

Calero et al., "Distinct properties of wild-type and the amyloidogenic human cystatin C variant of hereditary cerebral hemorrhage with amyloidosis, Icelandic type," J of Neurochemistry (2001) 77:628-637.

Carro et al., "Serum insulin-like growth factor I regulates brain amyloid-beta levels," Nat Med, vol. 8, pp. 1390-1397, 2002.

Castillo G.M., "Perlecan binds to the beta-amyloid proteins (A beta) of Alzheimer's disease, accelerates A beta fibril formation, and maintains A beta fibril stability," J Neurochem., vol. 69(6), pp. 2452-2465, 1997.

Chesebro et al., "Identification of scrapie prion protein-specific mRNA in scrapie-infected and uninfected brain," Nature (1985) 315:331-333.

Conway 2000. "Fibrils Formed in Vitro from a-Synuclein and Two Mutant Forms Linked to Parkinson's Disease are Typical Amyloid," Biochemistry 39:2552-2563.

Deierkauf et al., "Phygocytosis by rabbit polymorphonuclear leukocytes: the effect of albumin and polyamine acids on latex uptake," J. Cell Physiol. (1977) 92:169-175.

Demattos et al., "Clusterin promotes amyloid plaque formation and is critical for neuritic toxicity in a mouse model of Alzheimer's disease," Proc Natl Acad Sci USA, vol. 99, pp. 10843-10848, 2002.

Di Nicola et al., "Large-scale feasibility of gene transduction into human cd34+cell-derived dendritic cells by adenoviral/polycation complex," Brit. J. of Haematology (2000) 111:344-350.

Farmer et al., 1993. "Human immune response to cationized proteins. II. Characterization of interaction of cationized diphtheria toxoid with human mononuclear cells," Cellular Immunulogy 146(1):198-209.

Findeis, "Approaches to discovery and characterization of inhibitors of amyloid β-peptide polymerization," Biochim Biophys Acta (2000) 1502:76-84.

Frenkel et al., "High affinity binding of monoclonal antibodies to the sequential epitope EFRH of beta-amyloid peptide is essential for modulation of fibrillar aggregation," J Neuroimmunol (1999) vol. 95, pp. 136-142.

Frenkel et al., "Modulation of Alzheimer's β-Amyloid Neurotoxicity by Site-Directed Single-Chain Antibody," Neuroimmunomodulation (1999) 6:444 (p. 43).

Friedman et al. "Surfactant Effects on Amyloid Aggregation Kinetics," Journal of Molecular Biology 414:303-312 (2011).

Futaki et al., "Arginine-rich peptides: an abundant source of membrane-permeable peptides having potential as carriers for intracellular protein delivery," J. of Biological Chem. (2001) 276:5836-5840.

Gasset, M. et al. "Perturbation of the secondary structure of the scrapie prion protein under conditions that alter infectivity," Proc. Natl Acad. Sci. USA vol. 90, pp. 1-5. (1993).

Gellermann et al. "Aβ-globulomers are formed independently of the fibril pathway," (2008) Neurobiology of Disease 30:212-220.

Ghanta et al., 1996. "A strategy for designing inhibitors of β-amyloid toxicity," J. Biol. Chem. 271(47): 29525-29528.

Ghersi-Egea et al., "Fate of cerebrospinal fluid-borne amyloid β-peptide: rapid clearance into blood and appreciable accumulation by cerebral arteries," J Neurochem, vol. 67(2), pp. 880-883, 1996.

Ghetti et al., "Vascular variant of prion protein cerebral amyloidosis with τ-positive neurofibrillary tangles: the phenotype of the stop codon 145 mutation in PRNP," Proc Natl Acad Sci USA (1996) 93:744-748.

Ghetti et al., "Familial Gerstmann-Sträussler-Scheinker disease with neurofibrillary tangles," Mol Neurobiol (1994) 8:41-48.

Ghiso et al. "Alzheimer's soluble amyloid β is a normal component of human urine," FEBS Letters, vol. 408, pp. 105-108, 1997.

Ghiso et al., "The cerebrospinal-fluid soluble form of Alzheimer's amyloid beta is complexed to SP-40,40 (apolipoprotein J), an inhibitor of the complement membrane-attack complex," Biochem J, vol. 293, pp. 27-30, 1993.

(56) References Cited

OTHER PUBLICATIONS

Ghiso et al., "Unifying features of systemic and cerebral amyloidosis," Mol Neurobiol.,vol. 8, pp. 49-64, 1994.
Giasson et al., "Neuronal alpha-synucleinopathy with severe movement disorder in mice expressing A53T human alpha-synuclein," Neuron (2002) 34:521-533.
Goedert et al., "Alpha-Synuclein and neurodegenerative diseases," Nat Rev Neurosci (2001) 2:492-501.
Goni et al., Immunomodulation Targeting Abnormal Protein Conformation Reduces Pathology in a Mouse Model of Alzheimer's Disease, PLoS One 5(10): 1-3 (2010).
Goni, F. et al. "High titers of mucosal and system anti-PrP Antibodies Abrogate Oral Prior Infection in Mucosal-Vaccinated Mice", Neurosci. 153:679-686 (2008).
Goni, F. et al., "Mucosal vacccination delays or prevents prior infection via an oral route", Neurosci. 133:413-421 (2005).
Habicht et al., "Directed selection of a conformational antibody domain that prevents mature amyloid fibril formation by stabilizing Aβ protofibrils," PNAS 1 04(49): 19232-19237 (2007).
Hayden et al. "Amyloid β-protein oligomers and Alzheimer's disease," Alzheimer's Research & Therapy 5:60 (2013).
Helenius et al. "Solubilization of Membranes by Detergents," Biochimica et Biophysica Acta 415:29-79 (1975).
Hillen et al. "Generation and Therapeutic Efficacy of Highly Oligomer-Specific β-Amyloid Antibodies," The Journal of Neuroscience 30(31):10369-10379 (2010).
Holt et al. "Domain antibodies: proteins for therapy," Trends in biotech 21 (11):484-490 2003.
Horwich et al., "Deadly Conformations-Protein Misfolding in Prion Disease," Cell (1997) 89:499-510.
Hsiao et al., "Serial transmission in rodents of neurodegeneration from transgenic mice expressing mutant prion protein," Proc Natl Acad Sci USA (1994) 91:9126-9130.
International Search Report and Written Opinion of the International Searching Authority dated Oct. 4, 2012, which issued during prosecution of International Application No. PCT/US12/47424.
International Search Report for PCT/US03/40744, dated Jan. 26, 2006.
International Search Report and Written Opinion for corresponding PCT/US2012/046941 (Jan. 30, 2013).
Jackson DC et al., Free Radical Induced Polymerization of Synthetic Peptides into Polymeric Immunogens, Vaccine, 15(15): 1697-1705 (1997).
Jarrett et al. "The carboxy terminus of the beta amyloid protein is critical for the seeding of amyloid formation: implications for the pathogenesis Alzheimer's disease," Biochemistry, vol. 32, pp. 4693-4697 (1993).
Jarrett et al., "Seeding one-dimensional crystallization of amyloid: a pathogenic mechanism in Alzheimer's disease and scrapie?" Cell, vol. 73, pp. 1055-1058, (1993).
Ji et al., "Amyloid β40/42 clearance across the blood-brain barrier following intraventricular injections in wild-type, apoE knock-out and human apoE3 or E4 expressing transgenic mice," Journal of Alzheimer's Disease, vol. 3, pp. 23-30, 2001.
Johnson et al., "Islet amyloid, islet amyloid polypeptide, and diabetes mellitus," N Engl J Med 321:513-518 (1989).
Jordan J., "Isoform-Specific Effect of Apolipoprotein E on Cell Survival and beta-Amyloid-Induced Toxicity in Rat Hippocampal Pyramidal Neuronal Cultures," J. Neurosci., vol. 18, No. 1, pp. 195-204, 1998.
Kayed et al 2007 "Fibril specific, conformation dependent antibodies recognize a generic epitope common to amyloid fibrils and fibrillar oligomers that is absent in prefibrillar oligomers," Molec Neurodegen 2(18):1-11.
Kaytor et al., "Aberrant Protein Deposition and Neurological Disease," J Biol Chem (1999) 274:37507-37510.
Kisilevsky et al., "Anti-amyloid drugs: Potential in the treatment of diseases associated with aging," Drugs & Aging (1996) 8:75-83.

Klyubin et al., "Amyloid beta protein dimer-containing human CSF disrupts synaptic plasticity: prevention by systemic passive immunization," J Neurosci. (2008) vol. 28, No. 16, pp. 4231-4237.
Koudinov et al., "The soluble form of Alzheimer's amyloid beta protein is complexed to high density lipoprotein 3 and very high density lipoprotein in normal human plasma," Biophys Res Commun, vol. 205, No. 2, pp. 1164-1171, 1994.
Kretzschmar et al., "Scrapie prion proteins are synthesized in neurons", Am J Pathol (1986) 122:1-5.
Lauren, J. et al., Cellular Prior Protein Mediates Impairment of Synaptic Plasticity by Amyloid-Beta Oligomers, Nature, 457: 1128-1132 (Feb. 2009).
Levine, H., "Soluble multimeric Alzheimer beta(1-40) pre-amyloid complexes in dilute solution", Neurobiol. Aging. 16(5): 755-764 (1995).
Lowenadler 1990. "Enhanced immunogenicity of recombinant peptide fusions containing multiple copies of a heterologous T helper epitope." European Journal of Immunology 20:1541-1545.
Maillere, et al., 1995. "Fine chemical modifications at N- and C-termini enhance peptide presentation to T cells, by increasing the lifespan of both free and MHC-complexed peptides". Molecular Immunology 32(17/18): 1377-1385.
Martinez-Fong et al., "Nonenzymatic glycosylation of poly-L-lysine: a new tool for targeted gene delivery", Hepatology, (1994) 20:1602-1608.
Matsubara, et al. "Characterization of Apolipoprotein J-Alzheimer's Aβ Interaction," The Journal of Biological Chemistry, vol. 270, No. 13, pp. 7563-7567, 1995.
Matsuoka, Y., "Novel Therapeutic Approach for the Treatment of Alzheimer's Disease by Peripheral Administration of Agents with an Affinity to beta-Amyloid," J. Neurosci, vol. 23, No. 1. pp. 29-33, 2003.
Migneault et al. "Glutaraldehyde: behavior in aqueous solution, reaction with proteins, and application to enzyme crosslinking" (2004) BioTechniques 37:790-802.
Montserret et al. "Involvement of Electrostatic Interactions in the Mechanism of Peptide Folding Induced by Sodium Dodecyl Sulfate Binding" (2000) Biochemistry, 39(29):8362-8373.
Moore BD et al., "Biophysical analyses of synthetic amyloid-beta(1-42) aggregates before and after covalent cross-linking. Implications for deducing the structure of endogenous amyloid-beta oligomers", Biochem. 48:11796-11806 (2009).
Moriarty et al., "Effects of Sequential Proline Substitutions on Amyloid Formation by Human Amylin" Biochemistry (1999) 38:1811-1818.
Nielsen et al. "Unfolding of β-Sheet Proteins in SDS", (2007) Biophysical Journal 92:3674-3685.
Oesch et al., "A cellular gene encodes scrapie PrP 27-30 protein." Cell (1985) 40:735-746.
O'Nualiain and Wetzel "Conformational Abs recognizing a generic amyloid fibril epitope" PNAS 99(3):1485-1490 (2002).
Pallitto et al., "Recognition Sequence Design for Peptidyl Modulators of β-Amyloid Aggregation and Toxicity" Biochemistry (1999) 38:3570-3578.
Pepys et al., "Targeted Pharmacological Depletion of Serum Amyloid P Component for Treatment of Human Amyloidosis," Nature, vol. 417, pp. 254-259, 2002.
Permanne et al, "Detection of apolipoprotein E/Dimeric Soluble Amyloid J3 Complexes in Alzheimer's Disease Brain Supernatants," Biochemical and Biophysical Research Communications, vol. 240, pp. 715-720, 1997.
Peterson et al., "Polyamino Acid Enhancement of Bacterial Phagocytosis by Human Polymorphonuclear Leukocytes, and Peritoneal Macrophages", Infection and Immunity (1984) 43:561-566.
Pike, et al., 1993. "Neurodegeneration induced by beta-amyloid peptides in vitro: the role of peptide assembly state". J. Neuroscience 13(4) 1676-1687.
Poduslo et al., "beta-sheet Breaker Peptide Inhibitor of Alzheimer's Amyloidogenesis with Increased Blood-Brain Barrier Permeability and Resistance to Proteolytic Degradation in Plasma", J. Neurobiol., 1999, 371-382.

(56) References Cited

OTHER PUBLICATIONS

Prusiner et al., "Ablation of the Prion Protein (PrP) Gene in Mice Prevents Scrapie and Facilitates Production of Anti-PrP Antibodies," Proc Natl Acad Sci USA (1993) 90:10608-10612.
Prusiner et al., "Prion Protein Biology", Cell (1998) 93:337-348.
Quist A. et al., Amyloid ion channels: A common structural link for proteinmisfolding disease. PNAS, 102(30): 10427-10432 (2005).
Rubinsztein et al., "Intracellular inclusions, pathological markers in diseases caused by expanded polyglutamine tracts?", J Med Genet (1999) 36:265-270.
Sadler et al., "Synthetic Peptide Epitope-Based Polymers: Controlling Size and Determining the Efficiency of Epitope Incorporation", J. Pept. Res 60(3):150-158 (2002).
Sadowski et al., "A synthetic peptide blocking the apolipoprotein E/beta-amyloid binding mitigates beta-amyloid toxicity and fibril formation in vitro and reduces beta-amyloid plaques in transgenic mice," Am J Pathol. (2004) vol. 165, No. 3, pp. 937-948.
Sadowski et al., "Blocking the apolipoprotein E/amyloid-beta interaction as a potential therapeutic approach for Alzheimer's disease," Proc Natl Acad Sci U S A. (2006) vol. 103, No. 49, pp. 18787-18792. Epub Nov. 20, 2006.
Sadowski et al., "Disease modifying approaches for Alzheimer's pathology," Curr Pharm Des. (2007) vol. 13 No. 19, pp. 1943-1954.
Sadowski et al., "Targeting prion amyloid deposits in vivo," J Neuropathol Exp Neurol. (2004) vol. 63, No. 7, pp. 775-784.
Schenk et al., Immunization with amyloid-beta attenuates Alzheimer-disease-like pathology in the PDAPP mouse. Nature (1999) 400:173-177.
Schwarzenberger et al., "Poly-L-lysine-based molecular conjugate vectors: a high efficiency gene transfer system for human progenitor and leukemia cells.", Amer. J. of the Medical Sciences (2001) 321:129-136.
Serpell et al., "Fiber diffraction of synthetic α-synuclein filaments shows amyloid-like cross-β conformation", Proc Natl Acad Sci USA (2000) 97:4897-4902.
Seubert et al., "Isolation and quantification of soluble Alzheimer's beta-peptide from biological fluids," Nature, vol. 359, pp. 325-327, 1992.
Shen et al., "Disulfide spacer between methotrexate and poly(D-lysine). A probe for exploring the reductive process in endocytosis", J. of Biol. Chem. (1985) 260:10905-10908.
Shibata et al., "Clearance of Alzheimer's amyloid-$\beta_{1-40}$ peptide from brain by LDL receptor related protein-1 at the blood-brain barrier," J Clin Invest, vol. 106, pp. 1489-1499, 2000.
Shoji et al., "Production of the Alzheimer amyloid beta protein by normal proteolylic processing," Science, vol. 258, pp. 126-129, 1992.
Sigurdsson et al., "An attenuated immune response is sufficient to enhance cognition in an Alzheimer's disease mouse model immunized with amyloid-beta derivatives," J Neurosci. (2004) vol. 24, No. 28, pp. 6277-6282.
Sigurdsson et al., "Immunization delays the onset of prion disease in mice.", Amer. Journal of Pathology (2002) 161:13-17.
Sigurdsson et al., "Immunization for Alzheimer's Disease," Drug Development Research (2002) 56:135-142.
Sigurdsson et al., "Immunization with a nontoxic/nonfibrillar amyloid-β homologous peptide reduces Alzheimer's Disease-associated pathology in transgenic mice." Amer. Journal of Pathology (2001) 159:439-447.
Sigurdsson et al., "In Vivo Reversal of Amyloid-β Lesions in Rat Brain," J. of Neuropathology and Exp. Neurology (2000) 59:11-17.
Sigurdsson et al., "Infectivity of amyloid diseases", Trends in Mol. Medicine (2002) 8:411-413.
Simons et al. "Formation of protein micelles from amphiphilic membrane proteins" (1978) Proc. Natl. Acad. Sci. 75(11):5306-5310.
Solomon et al., "Disaggregation of Alzheimer β-amyloid by site-directed mAb",Proc. Natl. Acad. Sci. USA (1997) 94:4109-4112.

Soto et al., "β-sheet breaker peptides inhibit fibrillogenesis in a rat brain model of amyloidosis: Implications for Alzheimer's therapy," Nat Med (1998) 4:822-826.
Soto et al., "Reversion of prion protein conformational changes by synthetic beta-sheet breaker peptides." Lancet (2000) 355:192-197.
Spillantini et al., "Alpha-synuclein in Lewy bodies", Nature (1997) 388:839-840.
Stratagene Catalog, p. 215 (1991).
Tagliavini et al., "Synthetic peptides homologous to prion protein residues 106-147 form amyloid-like fibrils in vitro", Proc. Natl. Acad. Sci. USA (1993) 90:9678-9682.
Telling et al., "Interactions between wild-type and mutant prion proteins modulate neurodegeneration in transgenic mice." Genes & Dev (1996) 10:1736-1750.
Tew et al. "Stabilization of Neurotoxic Soluble β-Sheet-Rich Conformations of the Alzheimer's Disease Amyloid-β Peptide" (2008) Biophysical Journal 94:2752-2766.
Trouche et al., "Antibody response and plasma Aβ1-40 levels in young *Microcebus murinus* primates immunized with Aβ1-42 and its derivatives" Vaccine (2009) vol. 27, No. 7, pp. 957-964. Epub Dec. 27, 2008.
Tsigelny IF et al., Mechanisms of hybrid oligomer formation in the pathogenesis of combined Alzheimer's and Parkinson's diseases. PLoS One, 3(9):e3135, pp. 1-15 (2008).
Van Regenmortel et al. "D-peptides as Immunogens and Diagnostic Reagents," 1998. Current Opinion in Biotechnology 9:377-382.
Vickers et al., "A vaccine against Alzheimer's disease: developments to date," Drugs Aging, vol. 197(7), pp. 487-494, 2002.
Wahlström et al. "Secondary structure conversions of Alzheimer's Aβ(1-40) peptide induced by membrane-mimicking detergents" (2008) FEBS Journal 275:5117-5128.
Wang et al., 1989. "Endocytosis of Horseradish Peroxidase-Poly-Lysine Conjugate by Glomerular Epithelial Cells: An in vivo Study". J Pathol 159: 159-167.
Westermark et al., "Islet Amyloid Polypeptide: Pinpointing Amino Acid Residues Linked to Amyloid Fibril Formation," Proc Natl Acad Sci USA (1990) 87:5036-5040.
Wisniewski and Sigurdsson, 2002. "Immunization treatment approaches in Alzheimer's and prion diseases". Curr Neurol and Neurosci Rpts 2(2):400-404.
Wisniewski et al. "Immunotherapy for Alzheimer's Disease" (2014) Biochemical Pharmacology 88:499-507.
Wisniewski et al., "Amyloid-beta immunisation for Alzheimer's disease," Lancet Neurol. (2008) vol. 7, No. 9, pp. 805-811. Epub Jul. 28, 2008.
Wisniewski et al., "Immunological and anti-chaperone therapeutic approaches for Alzheimer disease," Brain Pathol. (2005) vol. 15, No. 1, pp. 72-77.
Wisniewski et al., "Immunomodulation for prion and prion-related diseases," Expert Rev Vaccines. (2010) vol. 9, No. 12, pp. 1441-1452.
Wisniewski et al., "Immunotherapeutic approaches for Alzheimer's disease in transgenic mouse models," Brain Struct Funct. (2010) vol. 214, Nos. 2-3, pp. 201-218. Epub Dec. 10, 2009.
Wisniewski et al., "Murine models of Alzheimer's disease and their use in developing immunotherapies," Biochim Biophys Acta. (2010) vol. 1802, No. 10, pp. 847-859. Epub May 13, 2010.
Wisniewski et al., "Preventing beta-amyloid fibrillization and deposition: beta-sheet breakers and pathological chaperone inhibitors," BMC Neurosci. (2008) vol. 3, No. 9, Suppl 2:S5.
Wisniewski et al., "Therapeutic approaches for prion and Alzheimer's diseases," FEBS J. (2007) vol. 274, No. 15, pp. 3784-3798. Epub Jul. 6, 2007.
Wisniewski et al., "Vaccination as a therapeutic approach to Alzheimer's disease," Mt Sinai J Med. (2010) vol. 77, No. 1, pp. 17-31.
Wisniewski et al., 2002. "Therapeutics in Alzheimer's and Prion Diseases". Biochemical Society Transactions 30: 574-578.
Wisniewski et al., "Short Communication: Acceleration of Alzheimer's Fibril Formation by Apolipaprotein E In Vitro," American Journal of Pathology, vol. 145, No. 5, pp. 1030-1035, 1994.
Wisniewski, "AD vaccines: conclusions and future directions," CNS Neurol Disord Drug Targets (2009) vol. 8, No. 2, pp. 160-166.

(56) References Cited

OTHER PUBLICATIONS

Wisniewski, et al. "Immunotherapy Targeting Abnormal Protein Conformation" Alzheimer's & Dementia 5(4) Suppl. 1:P113, Abstract #02-05-03, 2009.
Wong PT, Characterization of amyloid-beta interactions at the membrane interface: Implications for Pathogenesis. Doctoral dissertation, University of Michigan, pp. 41-48 (2009).
Wood et al., "Prolines and amyloidogenicity in fragments of the Alzheimer's peptide beta/A4", Biochemistry (1995) 34:724-730.
Yamada et al., "Complementary DNA for the mouse homolog of the human amyloid beta protein precursor," Biochem. Biophys. Res. Commun., 149:665-671,1987.
Yang et al., "Blocking the apolipoprotein E/amyloid-β interaction reduces fibrillar vascular amyloid deposition and cerebral microhemorrhages in TgSwDI mice," J Alzheimers Dis. (2011) vol. 24, No. 2, pp. 269-285.
Yankner, et al., 1990. "Neurotrophic and neurotoxic effects of amyloid beta protein: reversal by tachy kinin neuropeptides". Science 250(4978): 279-282.
Ylera et al., "Selection of RNA Aptamer to the Alzheimer's disease amyloid peptide," Biochem. Biophys. Res. Comm. , vol. 290, pp. 1583-1588, 2002.
Yu et al. "Structural Characterization of a Soluble Amyloid β-Peptide Oligomer" (2009) Biochemistry 48:1870-1877.
Zhou et al., "cDNA sequence of the 3'-coding region of PVY genome (the Chinese isolate)," Nucleic Acids Res., 18:5554, 1990.
Zlokovic et al. "Brain uptake of circulating apolipoproteins J and E complexed to Alzheimer's amyloid beta," Biochem Biophys Res Commun, vol. 205, pp. 1431-1437, 1994.
Zlokovic et al., "Glycoprotein 330/megalin: probable role in receptor-mediated transport of apolipoprotein J alone and in a complex with Alzheimer's disease amyloid? at the blood-brain and blood-cerebrospinal fluid barriers," Proc Natl Acad Sci USA, vol. 93, pp. 4229-4234, 1996.

* cited by examiner

Locomotor Testing TgSwDI

Locomotor Testing Tg 3x

A.

B.

C.

D.

Tg3x Vaccination

A.

B.

A.

B.

C.

D.

A.

B.

IMMUNOTHERAPEUTIC MODULATION OF AMYLOIDOGENIC DISEASE USING NON-FIBRILLOGENIC, NON-AMYLOIDOGENIC POLYMERIZED PROTEINS AND PEPTIDES

This application is a continuation of U.S. patent application Ser. No. 13/550,316, filed Jul. 16, 2012, which claims the benefit of U.S. Provisional Patent Application Ser. Nos. 61/509,320 and 61/509,442, both filed Jul. 19, 2011, which are hereby incorporated by reference in their entirety.

This invention was made with government support under grant numbers AG020245 and NS073501 awarded by the National Institutes of Health. The government has certain rights in the invention.

FIELD OF THE INVENTION

The present invention relates to pharmaceutical agents and antibodies suitable for the diagnosis, prevention, and treatment of amyloid disease.

BACKGROUND OF THE INVENTION

Amyloidosis broadly encompasses a variety of diseases that are characterized by the extracellular or intracellular deposition of amyloid proteins in tissues and/or organs. Amyloids are insoluble fibrous protein/peptide aggregates and their deposition may occur in localized sites or systemically. The fibrillar composition of these deposits is an identifying characteristic for the various forms of amyloid disease. In some cases the amyloid protein/peptide accumulates intracellullary, resulting in cell dysfunction and ultimately cell death. Examples of intracellular amyloid proteins include α-synuclein, forming Lewy bodies in Parkinson's disease, and huntingtin, forming neuronal inclusions in Huntington disease. The pathogenesis of Alzheimer's disease (AD), the most common of the amyloid related neurodegenerative disorders, is linked to the cleavage of the amyloid precursor protein generating the amyloid-β (Aβ) peptide which undergoes a shape change into a pathological conformer having a high β-sheet content. Intracerebral and cerebrovascular deposits composed primarily of fibrils of the pathological AB peptide are characteristic of both familial and sporadic forms of AD. In addition to Aβ, abnormally folded and phosphorylated tau protein forms toxic oligomeric structures and neurofibrillary tangles in AD. Similar to AD, prion-associated diseases, such as Creutzfeld-Jacob disease, have also been characterized as amyloid diseases. The pathogenesis of prion disease is linked to a change of the cellular prion protein ($PrP^C$) into the disease associated $PrP^{Sc}$ (Sc for scrapie). Currently, there is no effective therapy for any of these disorders.

An active area of translational research and current clinical trials for amyloid disease has focused on immunotherapy, using both passive and active immunization against amyloid proteins, particularly Aβ in AD (Wisniewski et al., "Amyloid-β Immunization for Alzheimer's Disease," *Lancet Neurol* 7:805-811 (2008)). Although immunotherapy holds great promise as a means of reducing amyloid deposition, it, unfortunately, has been accompanied by major obstacles. Specific problems associated with immunotherapy that were identified in a clinical trial for AD include the potential of toxicity from encephalitis (related to excessive cell mediated immunity), the immunological targeting of both the normal and abnormal Aβ peptide, the failure to address tau related pathology, and the apparent poor efficacy. Moreover, although autopsy data from this early immunotherapy vaccine trial suggested that many patients had a significant reduction in amyloid burden, these patients exhibited only minor cognitive benefits (Wisniewski et al., "Amyloid-β Immunization for Alzheimer's Disease," *Lancet Neurol* 7:805-811 (2008) and Holmes et al., "Long Term Effects of Aβ42 Immunization in Alzheimer's Disease: Immune Response, Plaque Removal and Clinical Function," *Lancet* 372:216-223 (2008)). Therefore, an immunotherapeutic approach that can effectively reduce amyloid burden and overcome the aforementioned problems is warranted.

The present invention is directed to overcoming these and other deficiencies in the art.

SUMMARY OF THE INVENTION

A first aspect of the present invention relates to a non-amyloidogenic, non-fibrillogenic polymerized product comprising two or more protein and/or peptide units, where each unit is independently selected from the group consisting of an amyloid-beta (Aβ) peptide, an α-synuclein protein or peptide, a tau protein or peptide, a TAR DNA-binding protein 43 (TDP-43) protein or peptide, an amylin protein or peptide, a prion protein (PrP) protein or peptide, and any combination thereof.

A second aspect of the present invention is directed to an isolated antibody or binding portion thereof having antigenic specificity for an epitope a non-amyloidogenic, non-fibrillogenic polymerized product. The polymerized product comprises two or more protein and/or peptide units, each unit independently selected from the group consisting of an amyloid-beta (Aβ) peptide, an α-synuclein protein or peptide, a tau protein or peptide, a TAR DNA-binding protein 43 (TDP-43) protein or peptide, an amylin protein or peptide, a prion protein (PrP) protein or peptide, and any combination thereof.

The development of an effective immunotherapeutic approach for the prevention and treatment of amyloid related diseases has been hindered by potential cell-mediated toxicity, non-specific immunological targeting of both normal and amyloidogenic proteins, and overall poor efficacy. The immunotherapeutic approach of the present invention employs non-amyloidogenic, non-fibrillogenic polymerized protein and/or peptides and co-polymerized proteins and/or peptides to generate a specific immunological response to conformational epitopes that are shared by various amyloidogenic proteins, thereby overcoming many of the above noted obstacles.

BRIEF DESCRIPTION OF THE DRAWINGS

FIG. 3A is a graph depicting the results of the radial arm maze. The number of errors (y-axis) versus the day of testing (x-axis) are plotted for 3×Tg mice vaccinated with polymerized ABri, transgenic control (Tg control), and wildtype. Vaccinated transgenic animals commit significantly fewer errors that non-treated transgenic and perform similarly to the wildtype animals. p=0.0044 one-way ANOVA; p<0.01 wildtype and Tg pABri treated vs. Tg control; p=>0.05 wildtype vs. Tg pABri treated. FIG. 3B is a similar graph showing the radial arm maze results for 3×Tg animals vaccinated with polymerized ABri, polymerized Aβ1-30$K_{18}K_{19}$, and the combination (polymerized ABri and Aβ1-30$K_{18}K_{19}$). All treatment groups committed significantly fewer errors than the transgenic control animals. p=0.004 by one-way ANOVA; p<0.01 all Tg Treated groups and wild-type versus Tg Control; no significant difference between wild-type and Tg treated groups. FIG. 3C is another graph depicting the results of the radial arm maze cognitive testing. In this graph the number of errors (y-axis) versus the day of testing (x-axis) are plotted for SwDI transgenic mice vaccinated with polymerized ABri, polymerized Aβ1-30$_{18}K_{19}$K, polymerized Aβ1-42, transgenic control mice, and wildtype mice (WT). All treatment groups committed significantly fewer errors than the transgenic control animals (p<0.01 all Tg Treated groups and wild-type versus Tg Control).

FIG. 6A is a bar graph showing the reduction of hippocampal amyloid burden in Tg3x animals administered polymerized ABri (Tg-pABri), polymerized Aβ1-30$_{18}K_{19}$K (Tg-AB1-30KK), or the combination of polymerized peptides (Tg-combined) compared to transgenic control (Tg-control) animals (p=0.001 by one way ANOVA post-hoc testing; p<0.01 all treatment groups vs. control). FIGS. 6B and 6C show a reduction in PHF1 in the hippocampus and cortex, respectively, of Tg3x animals administered polymerized ABri or the combination of polymerized ABri and Aβ1-30$_{18}K_{19}$K (p<0.0001 one way ANOVA post hoc; p<0.001 Tg-ABri and Tg-combined vs. Tg-control and Tg-Aβ1-30$_{18}K_{19}$K for both hippocampal and cortical analyses). No significant difference was found between Tg-control and Tg-Aβ1-30$_{18}K_{19}$K treated animals.

FIG. 7A is a bar graph showing the reduction in hippocampal amyloid burden in polymerized ABri vaccinated (Tg pABri), polymerized Aβ1-30$_{18}K_{19}$K vaccinated (Tg-Aβ1-30KK), and polymerized Aβ1-42 vaccinated (Tg-Aβ42) animals compared to transgenic control (Tg Control). FIG. 7B is an electron micrograph (EM) image of negatively stained polymerized Aβ1-42 peptide, which is predominately in the form of spherical particles of ~200 nm.

In FIG. 8A Aβ1-42 peptide was aged for 3 months after controlled polymerized with glutaraldehyde. There is no evidence of fibril formation, and the sample was typical of oligomerized peptides/proteins. FIG. 8B is an Aβ1-42 peptide from the same synthesis batch as the peptide in FIG. 8A. This peptide was dissolved in saline and aged for 3 months before the EM. In contrast to the polymerized Aβ1-42 peptide, the unpolymerized Aβ1-42 sample was completely fibrillized.

DETAILED DESCRIPTION OF THE INVENTION

Figure 1A:
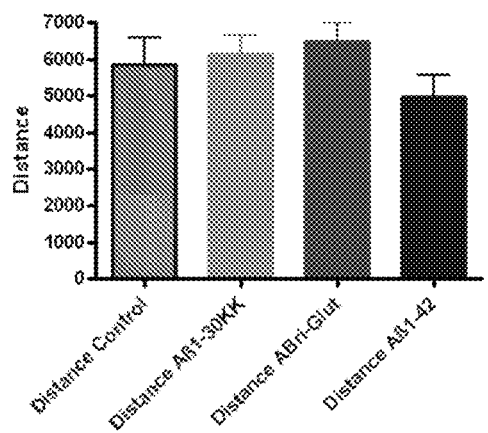
FIGS. 1A-1D show the results of locomotor activity testing in SwDI transgenic (Tg) control mice and Tg mice vaccinated with synthetic polymerized Aβ peptide (Aβ1-$30_{18}K_{19}K$), polymerized ABri peptide (ABri-Glut), or polymerized Aβ1-42 peptide. No significant differences between the groups were noted in distance traveled (FIG. 1A) or mean velocity (Vmean) (FIG. 1C). Aβ1-42 vaccinated Tg mice exhibited slower maximum velocity (Vmax) (FIG. 1B) (p=0.0234 post-hoc only; Aβ1-42 versus control p<0.05) and longer resting time (FIG. 1D) (p=0.0311 post-hoc only; Aβ1-42 versus control p<0.05) compared to controls. No significant differences between the Aβ1-$30_{18}K_{19}K$ and ABri treated Tg animals and controls in these parameters were observed (FIGS. 1B and 1D)

A first aspect of the present invention relates to a non-amyloidogenic, non-fibrillogenic polymerized product comprising two or more protein and/or peptide units, where each unit is independently selected from the group consisting of an amyloid-beta (Aβ) peptide, an α-synuclein protein or peptide, a tau peptide or peptide, a TAR DNA-binding protein 43 (TDP-43) protein or peptide, an amylin protein or peptide, a PrP protein or peptide, and any combination thereof.

In accordance with this aspect of the invention suitable AB peptides of the polymerized product include, without limitation, Aβ1-42 and peptides derived therefrom. The amino acid sequence of Aβ1-42 is provided as SEQ ID NO: 1 below.

```
                                              (SEQ ID NO: 1)
daefrhdsgy evhhgklvff aedvgsnkga iiglmvggvv ia
```

Accordingly, in one embodiment of the invention, the AB peptide of the polymerized product comprises amino acid residues 1-42 of SEQ ID NO: 1. Alternatively suitable Aβ peptides of the polymerized product include, without limitation, peptides comprising amino acid residues 1-16 of SEQ ID NO: 1, amino acid residues 1-20 of SEQ ID NO: 1, amino acid residues 1-30 of SEQ ID NO:1, amino acid residues 1-40 of SEQ ID NO: 1, amino acid residues 1-42 of SEQ ID NO: 1, amino acid residues 10-30 of SEQ ID NO: 1, amino acid residues 20-40 of SEQ ID NO: 1, and amino acid residues 20-42 of SEQ ID NO: 1.

In another embodiment of the present invention, the Aβ peptide of the polymerized product contains two amino acid substitutions at amino acid residues 18 and 19 of SEQ ID NO: 1. In one embodiment the amino acid substitutions comprise a valine to lysine substitution at position 18 and a phenylalanine to lysine substitution at position 19 of SEQ ID NO: 1. Peptides having these two amino acid substitutions are referred to as AβK$_{18}$K$_{19}$ peptides and are derived from the amino acid sequence of SEQ ID NO:2 below.

```
                                              (SEQ ID NO: 2)
daefrhdsgy evhhqklkkf aedvgsnkga iiglmvggvv ia
```

Accordingly, suitable Aβ peptides comprising the double lysine substitution include, without limitation, peptides comprising amino acid residues 1-30 of SEQ ID NO:2 (Aβ1-30K$_{18}$K$_{19}$), amino acid residues 1-40 of SEQ ID NO:2 (Aβ1-40K$_{18}$K$_{19}$), amino acid residues 1-42 of SEQ ID NO:2 (Aβ1-42K$_{18}$K$_{19}$), amino acid residues 1-20 of SEQ ID NO:2 (Aβ1-20K$_{18}$K$_{19}$), amino acid residues 10-30 of SEQ ID NO:2 (Aβ10-30K$_{18}$K$_{19}$), amino acid residues 10-40 of SEQ ID NO:2 (A 310-40K$_{18}$K$_{19}$), amino acid residues 10-42 of SEQ ID NO:2 (Aβ10-42K$_{18}$K$_{19}$), amino acid residues 20-40 of SEQ ID NO:2 (Aβ20-40K$_{18}$K$_{19}$), and amino acid residues 20-42 of SEQ ID NO:2 (Aβ20-42K$_{18}$K$_{19}$).

The polymerized product of the present invention may comprise a homopolymer of an Aβ peptide or a copolymer of two or more different AB peptides. Alternatively, the polymerized product of the present invention may comprise a copolymer of an Aβ protein or peptide co-polymerized with any one or more of an α-synuclein protein or peptide, a tau protein or peptide, a TDP-43 protein or peptide, an amylin protein or peptide, and/or a PrP protein or peptide. In one embodiment of the present invention, the polymerized product comprises a copolymer of one or more Aβ peptides copolymerized with one or more α-synuclein proteins or peptides. In another embodiment of the present invention, the polymerized product comprises a copolymer of one or more AB peptides copolymerized with one or more tau proteins or peptides. In another embodiment of the present invention, the polymerized product comprises a copolymer of one or more Aβ peptides copolymerized with one or more TDP-43 proteins or peptides The polymerized product of the present invention may also comprise an α-synuclein protein or peptide thereof. The α-synuclein protein comprises the amino acid sequence of SEQ ID NO:3.

```
                                                              (SEQ ID NO: 3)
  1  mdvfmkglsk akegvvaaae ktkqgvaeaa gktkegvlyv gsktkegvvh gvatvaektk
 61  eqvtnvggav vtgvtavaqk tvegagsiaa atgfvkkdql gkneegapqe giledmpvdp
121  dneayempse egyqdyepea
```

Accordingly, in one embodiment of the invention, the α-synuclein protein of the polymerized product comprises amino acid residues 1-140 of SEQ ID NO:3. Peptides of α-synuclein derived from the amino acid sequence of SEQ ID NO: 3 are also suitable for use in the polymerized product of the present invention. In one embodiment, the peptide comprises at least five contiguous amino acids of SEQ ID NO:3. In another embodiment, the peptide comprises at least 10, at least 15, at least 20, at least 25, at least 30, at least 35, at least 40, at least 45, at least 50, at least 55, at least 60, at least 65, at least 70, at least 75, at least 80, at least 90 or at least 100 contiguous amino acids of SEQ ID NO:3.

In one embodiment of the invention, the α-synuclein peptide is a C-terminal α-synuclein peptide as disclosed in WO 2004/041067 to Schenk at al., which is hereby incorporated by reference in its entirety. Suitable C-terminal α-synuclein peptides for use in the polymerized product of the present invention include, without limitation, peptides comprising amino acids residues 70-140 of SEQ ID NO:3, amino acid residues 100-140 of SEQ ID NO:3, amino acid residues 120-140 of SEQ ID NO:3, amino acid residues 130-140 of SEQ ID NO:3, or amino acid residues 135-140 of SEQ ID NO:3.

The polymerized product of the present invention may comprise a homopolymer of an α-synuclein protein or peptide or a copolymer of two or more different α-synuclein proteins or peptides. Alternatively, the polymerized product of the present invention may comprise a copolymer of an α-synuclein protein or peptide co-polymerized with any one or more of an AB peptide, a tau protein or peptide, a TDP-43 protein or peptide, an amylin protein or peptide, and/or a PrP protein or peptide.

The pharmaceutical composition of the present invention may also comprise a tau protein or peptide thereof. Suitable tau proteins of the present invention include any of the eight isoforms of the human tau protein that are known in the art (see NCBI Accession Nos. NP_058519.3, NP_005901, NP_058518.1, NP_058525.1, NP_001116539.1, NP_001116538.2, NP_001190180.1, and NP_001190181.1, which are hereby incorporated by reference in their entirety).

The tau isoforms vary in the number of N-terminal inserts resulting from the splicing of exons two and three, and microtubule-binding domains resulting from the splicing of exon ten. The amino acid sequence corresponding to human tau protein isoform 2 (441a.a), containing two N-terminal inserts and four microtubule binding (2N4R) domains is provided as SEQ ID NO:4 below.

```
                                                        (SEQ ID NO: 4)
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65              70                  75                  80

Asp Glu Gly Ala Pro Gly Lys Gln Ala Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
            210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365
```

-continued

```
Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
```

Accordingly, in one embodiment, a tau protein of the polymerized product of the present invention comprises amino acid residues 1-441 of SEQ ID NO:4. Alternatively, the composition of the invention comprises amino acid residues 1-758 of tau isoform 1 (NP_058519.3), amino acid residues 1-383 of tau isoform 3 (NP_058518.1), amino acid residues 1-352 of tau isoform 4 (NP_058525.1), amino acid residues 1-412 of tau isoform 5 (NP_001116539.1), amino acid residue 1-776 of tau isoform 6 (NP_001116538.2), amino acid residues 1-381 of tau isoform 7 (NP_001190180.1), and amino acid residues 1-410 of tau isoform 8 (NP_001190181.1).

The pharmaceutical composition of the present invention may also comprise tau peptides derived from the amino acid sequence of SEQ ID NO:4 or the amino acid sequence of any other tau isoform. In one embodiment, the tau peptide comprises at least five contiguous amino acids of a tau protein, e.g., the tau protein of SEQ ID NO:4. In another embodiment, the tau peptide comprises at least 10, at least 15, at least 20, at least 25, at least 30, at least 35, at least 40, at least 45, at least 50, at least 55, at least 60, at least 65, at least 70, at least 75, at least 80, at least 90, or at least 100 contiguous amino acids of a tau protein, e.g., the tau protein of SEQ ID NO:4. In yet another embodiment, the peptide comprises at least 200, at least 300, at least 400, or at least 500 contiguous amino acids, of a tau protein.

A number of tau peptides that are suitable for polymerization and incorporation into the polymerized product of the present invention are disclosed in U.S. Pat. No. 8,012,936 to Sigurdsson et al., which is hereby incorporated by reference in its entirety. Suitable peptides include, without limitation, amino acid residues 1-30 of SEQ ID NO:4, amino acid residues 30-60 of SEQ ID NO:4, amino acid residues 60-90 of SEQ ID NO:4, amino acid residues 90-120 of SEQ ID NO:4, amino acid residues 120-150 of SEQ ID NO:4, amino acid residues 150-180 of SEQ ID NO:4, amino acid residues 210-240 of SEQ ID NO:4, amino acid residues 270-300 of SEQ ID NO:4, amino acid residues 300-330 of SEQ ID NO:4, amino acid residues 330-360 of SEQ ID NO:4, amino acid residues 360-390 of SEQ ID NO:4, amino acid residues 390-420 of SEQ ID NO:4, amino acid residues 411-440 of SEQ ID NO:4, amino acid residues 133-162 of SEQ ID NO:4, amino acid residues 379-409 of SEQ ID NO:4, amino acid residues 192-221 of SEQ ID NO:4, amino acid residues 221-250 of SEQ ID NO:4, or amino acid residues 184-213 of SEQ ID NO:4.

The polymerized product of the present invention may comprise a homopolymer of tau protein or peptide or a copolymer of two or more different tau proteins or peptides. Alternatively, the polymerized product of the present invention may comprise a copolymer of a tau protein or peptide co-polymerized with any one or more of an Aβ peptide, an α-synuclein protein or peptide, a TDP-43 protein or peptide, an amylin protein or peptide, and/or a PrP protein or peptide.

The polymerized product of the present invention may also comprise a TAR DNA-binding protein 43 (TDP 43) or peptide thereof. The human TDP 43 protein comprises the amino acid sequence of SEQ ID NO:5.

(SEQ ID NO: 5)

```
  1  mseyirvted endepieips eddgtvllst vtaqfpgacg lryrnpvsqc mrgvrlvegi 61  lhapdagwgn lvyvvnypkd nkrkmdetda ssavkvkrav qktsdlivlg lpwktteqdl 121  keyfstfgev lmvqvkkdlk tghskgfgfv rfteyetqvk vmsqrhmidg rwcdcklpns 181  kqsqdeplrs rkvfvgrcte dmtedelref fsqygdvmdv fipkpfrafa fvtfaddqia 241  qslcgedlii kgisvhisna epkhnsnrql ersgrfggnp ggfgnqggfg nsrgggaglg 301  nnqgsnmggg mnfgafsinp ammaaaqaal qsswgmmgml asqqnqsgps gnnqnqgnmq 361  repnqafgsg nnsysgsnsg aaigwgsasn agsgsgfngg fgssmdskss gwgm
```

Accordingly, in one embodiment of the invention, the TDP-43 protein of the polymerized product comprises amino acid residues 1-414 of SEQ ID NO:5. Peptides of TDP-43 derived from the amino acid sequence of SEQ ID NO:5 are also suitable for use in the pharmaceutical composition of the present invention. In one embodiment, the TDP-43 peptide comprises at least five contiguous amino acids of SEQ ID NO:5. In another embodiment, the TDP-43 peptide comprises at least 10, at least 15, at least 20, at least 25, at least 30, at least 35, at least 40, at least 45, at least 50, at least 55, at least 60, at least 65, at least 70, at least 75, at least 80, at least 90, at least 100, at least 150, at least 200, at least 250, or at least 300 contiguous amino acids of SEQ ID NO:5.

The polymerized product of the present invention may comprise a homopolymer of a TDP-43 protein or peptide or a copolymer of two or more different TDP-43 proteins or peptides. Alternatively, the polymerized product of the present invention may comprise a copolymer of a TDP-43 protein or peptide co-polymerized with any one or more of an Aβ peptide, a tau protein or peptide, an α-synuclein protein or peptide, an amylin protein or peptide, and/or a PrP protein or peptide.

The polymerized product of the present invention can also comprise an amylin protein or peptide thereof. The human amylin protein comprises the amino acid sequence of SEQ ID NO:6.

```
                                                    (SEQ ID NO: 6)
  1   hgvekrkcnt atcatqrlan flvhssnnfg ailsstnvgs ntygkrnave vlkrepinyl 61   pl
```

Accordingly, in one embodiment of the invention, the amylin protein of the polymerized product comprises amino acid residues 1-62 of SEQ ID NO:6. Peptides of amylin derived from the amino acid sequence of SEQ ID NO:6 are also suitable for use in the pharmaceutical composition of the present invention. In one embodiment, the amylin peptide comprises at least five contiguous amino acids of SEQ ID NO:6. In another embodiment, the amylin peptide comprises at least 10, at least 15, at least 20, at least 25, at least 30, at least 35, at least 40, at least 45, at least 50, at least 55, at least 60 contiguous amino acids of SEQ ID NO:6.

The polymerized product of the present invention may comprise a homopolymer of an amylin protein or peptide or a copolymer of two or more different amylin proteins or peptides. Alternatively, the polymerized product of the present invention may comprise a copolymer of an amylin protein or peptide co-polymerized with any one or more of an Aβ peptide, a tau protein or peptide, an α-synuclein protein or peptide, a TDP-43 protein or peptide, and/or a PrP protein or peptide.

The polymerized product of the present invention may also comprise a prion protein or peptide thereof. The human prion protein comprises the amino acid sequence of SEQ ID NO:7.

tion may comprise a copolymer of an PrP protein or peptide co-polymerized with any one or more of an Aβ peptide, a tau protein or peptide, an α-synuclein protein or peptide, a TDP-43 protein or peptide, and/or an amylin protein or peptide as described herein.

The polymerized product of the present invention may further comprise one or more polymerized ABri peptides (CSRTVKKNIIEEN; SEQ ID NO: 8), ADan peptides (CFNLFLNSQEKHY; SEQ ID NO:9), or ABri/ADan fusion peptides (CSRTVKKNIIEENGSGSGCFNLFLNSQEKHY; SEQ ID NO: 10) as disclosed in U.S. Patent Application Publication No. 20100284909 to Wisniewski et al., which is hereby incorporated by reference in its entirety.

The proteins and peptides of the polymerized product of the present invention may comprise naturally occurring peptides or analog peptides. Analog peptides typically differ from naturally occurring peptides at one, two, or a few positions, often by virtue of conservative substitutions. Analogs typically exhibit at least 80 or 90% sequence identity with natural peptides. Some analogs include unnatural amino acids or modifications of N or C terminal amino acids at one, two or a few positions. Examples of unnatural amino acids are D-amino acids, alpha amino acids, alpha-disubstituted amino acids, N-alkyl amino acids, lactic acid, 4-hydroxyproline, gamma-carboxyglutamate, epsilon-N,N, N-trimethyllysine, epsilon-N-acetyllysine, O-phosphoserine, N-acetylserine, N-formylmethionine, 3-methylhistidine, 5-hydroxylysine, omega-N-methylarginine, f3-alanine, omithine, norleucine, norvaline, hydroxyproline, thyroxine, gamma-amino butyric acid, homoserine, citrulline, and isoaspartic acid. Analog peptides can be screened for pro-

```
                                                     (SEQ ID NO: 7)
  1   manlgcwmlv lfvatwsdlg lckkrpkpgg wntggsrypg qgspggnryp pqggggwgqp 61   hgggwgqphg ggwgqphggg wgqphgggwg qgggthsqwn kpskpktnmk hmagaaaaga 121   vvgglggyvl gsamsrpiih fgsdyedryy renmhrypnq vyyrpmdeys nqnnfvhdcv 181   nitikqhtvt tttkgenfte tdvkmmervv eqmcitqyer esqayykrgs smvlfssppv 241   illisflifl ivg
```

Accordingly, in one embodiment of the invention, the prion protein of the polymerized product comprises amino acid residues 1-253 of SEQ ID NO:7 or analogs thereof. Peptides of prion protein derived from the amino acid sequence of SEQ ID NO:7 are also suitable for use in the polymerized product of the present invention. In one embodiment, the peptide comprises at least five contiguous amino acids of SEQ ID NO:7. In another embodiment, the peptide comprises at least 10, at least 15, at least 20, at least 25, at least 30, at least 35, at least 40, at least 45, at least 50, at least 55, at least 60, at least 65, at least 70, at least 75, at least 80, at least 90 or at least 100, at least 125, and least 150, at least 200, or at least 225 contiguous amino acids of SEQ ID NO:7.

The polymerized product of the present invention may comprise a homopolymer of an PrP protein or peptide or a copolymer of two or more different PrP proteins or peptides. Alternatively, the polymerized product of the present invenphylactic or therapeutic efficacy using animal models as described in the Examples herein.

In another embodiment of the present invention, the polymerized product comprises a polymer of a fusion peptide. Suitable fusion peptides contain any first Aβ, α-synuclein, tau, TDP-43, amylin, or prion protein peptide of the present invention fused to any second Aβ, α-synuclein, tau, TDP-43, amylin, or prion protein peptide of the present invention. The fusion peptide preferably contains a short linker sequence coupling the first peptide to a second peptide. Preferred linker sequences include glycine-rich (e.g. $G_3$-5) or serine-rich (e.g. GSG, GSGS (SEQ ID NO: 13), GSGSG (SEQ ID NO: 14), $GS_NG$) linker sequences.

In accordance with this aspect of the present invention the polymerized product may contain a polymer or copolymer of any one or more of the AD, α-synuclein, tau, TDP-43, amylin, or prion protein proteins or peptides described herein further linked in-frame to an adjuvant polypeptide.

The adjuvant polypeptide can be any adjuvant polypeptide known in the art, including, but not limited to, cholera toxin B, flagellin, human papillomavirus L1 or L2 protein, herpes simplex glycoprotein D (gD), complement C4 binding protein, TL4 ligand, and IL-1β. The protein or peptides comprising the polymers of the polymerized product of the present invention may be linked directly to the adjuvant polypeptide or coupled to the adjuvant by way of a short linker sequence. Suitable linker sequences include glycine or serine-rich linkers described supra or other flexible immunoglobulin linkers as disclosed in U.S. Pat. No. 5,516,637 to Huang et al, which is hereby incorporated by reference in its entirety.

In another embodiment, the polymerized product of the present invention may contain a polymer or copolymer of any one of the Aβ, α-synuclein, tau, TDP-43, amylin, or prion protein proteins or peptides described supra conjugated to an immunogenic carrier molecule. The immunogenic carrier molecule can be covalently or non-covalently bonded to the proteins or peptides as described herein. Suitable immunogenic carrier molecules include, but are not limited to, serum albumins, chicken egg ovalbumin, keyhole limpet hemocyanin, tetanus toxoid, thyroglobulin, pneumococcal capsular polysaccharides, CRM 197, immunoglobulin molecules, alum, and meningococcal outer membrane proteins. Other suitable immunogenic carrier molecules include T-cell epitopes, such as tetanus toxoid (e.g., the P2 and P30 epitopes), Hepatitis B surface antigen, pertussis, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomersae, *Escherichia coli* TraT, and Influenza virus hemagluttinin (HA). Other suitable immunogenic carrier molecules include promiscuous T helper cell epitopes which are derived from hepatitis B virus, *Bordetella pertussis, Clostridium tetani, Pertusaria trachythallina, E. coli, Chlamydia trachomatis*, Diphtheria, *P. falciparum*, and *Schistosoma mansoni* (see U.S. Pat. No. 6,906,169 to Wang; U.S. Patent Application Publication No. 20030068325 to Wang, and WO 2002/096350 to Wang, which are hereby incorporated by reference in their entirety). Yet other suitable carriers include T-helper cell epitopes derived from tetanus toxin, cholera toxin B, pertussis toxin, diphtheria toxin, measles virus F protein, hepatitis B virus surface antigen, *C. trachomitis* major outer membrane protein, *P. falciparum* circumsporozoite, *S. mansoni* triose phosphate isomerase, or *E. coli* TraT (see WO01/42306 to Chain, which is hereby incorporated by reference in its entirety).

The peptides and proteins of the present invention can be linked to immunogenic carrier molecules by chemical cross-linking prior to polymerization. Techniques for linking a peptide immunogen to an immunogenic carrier molecule include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine residues on one protein, and an amide linkage through the epsilon-amino on a lysine, or other free amino group in other amino acids. A variety of such disulfide/amide-forming agents are described by Jansen et al., "Immunotoxins: Hybrid Molecules Combining High Specificity and Potent Cytotoxicity," *Immun Rev* 62:185-216 (1982), which is hereby incorporated by reference in its entirety. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, and 4-(N-maleimido-methyl)cyclohexane-1-carboxylic acid. The carboxyl groups can be activated by combining them with succinimide or 1-hydroxyl-2-nitro-4-sulfonic acid, sodium salt.

The one or more proteins or peptides comprising the polymers or copolymers of the polymerized product of the present invention can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES: A USERS GUIDE 93-210 (Gregory A. Grant ed., 1992), which is hereby incorporated by reference in its entirety). Protein or peptide production via recombinant expression can be carried out using bacteria, such as *E. coli*, yeast, insect or mammalian cells and expression systems. Procedures for recombinant protein/peptide expression are well known in the art and are described by Sambrook et al, Molecular Cloning: A Laboratory Manual (C.S.H.P. Press, NY 2d ed., 1989).

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Polymerization of the proteins or peptides alone or conjugated to an adjuvant polypeptide or immunogenic carrier molecule can be achieved using standard techniques known in the art. As used herein, polymerization refers to process of reacting two or more peptide and/or protein units together under suitable conditions to form three-dimensional networks or polymer chains. As described herein, the proteins and peptides can be polymerized by a reaction with a cross linking reagent. Suitable cross-linking reagents include, but are not limited to glutaraldehyde and 1-Ethyl-3-[3-dimethylaminopropyl]carbodiimide hydrochloride (EDC) (see Goni et al., "Immunomodulation Targeting Abnormal Protein Conformation Reduced Pathology in a Mouse Model of Alzheimer's Disease," *PLoS One* 5(10):e13391 (2010), which is hereby incorporated by reference in its entirety). Alternatively, the proteins and peptides can be polymerized by cysteine oxidation induced disulfide cross linking.

Another aspect of the present invention is directed to a pharmaceutical composition comprising the polymerized product of the invention and a pharmaceutical carrier.

In accordance with this aspect of the present invention, the pharmaceutical composition may contain a single homopolymer of an Aβ protein or peptide, α-synuclein protein or peptide, tau protein or peptide, TDP-43 protein or peptide, amylin protein or peptide, or prion protein or peptide. Alternatively, the pharmaceutical composition may contain a mixture of one or more proteins or peptides, i.e. heteropolymers of the one or more aforementioned proteins and/or peptides.

The pharmaceutical composition of the present invention can further contain, in addition to peptide polymers, other pharmaceutically acceptable components (see REMINGTON'S PHARMACEUTICAL SCIENCE (19th ed., 1995), which is hereby incorporated by reference in its entirety). The incorporation of such pharmaceutically acceptable components depends on the intended mode of administration and therapeutic application of the pharmaceutical composition. Typically, however, the pharmaceutical composition will include a pharmaceutically-acceptable, non-toxic carrier or diluent, which are defined as vehicles commonly used to formulate pharmaceutical compositions for animal or human administration. The diluent is selected so as not to affect the biological activity of the composition. Exemplary carriers or diluents include distilled water, physiological phosphate-buffered saline, Ringer's solutions, dextrose solution, and Hank's solution.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose), polymeric amino acids, amino acid copolymers, and lipid aggregates (such as oil droplets or liposomes).

The pharmaceutical composition of the present invention can further contain an adjuvant. One class of preferred adjuvants is aluminum salts, such as aluminum hydroxide, aluminum phosphate, or aluminum sulfate. Such adjuvants can be used with or without other specific immunostimulating agents such as MPL or 3-DMP, QS-21, flagellin, attenuated *Salmonella* (e.g., *Salmonella typhimurium*), polymeric or monomeric amino acids such as polyglutamic acid or polylysine, or pluronic polyols. Oil-in-water emulsion formulations are also suitable adjuvants that can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-A1-D-isoglu-L-Ala-dipalmitoxy propylamide (DTP-DPP) Theramide™, or other bacterial cell wall components). A suitable oil-in-water emulsion is MF59 (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.) as described in WO90/14837 to Van Nest et al., which is hereby incorporated by reference in its entirety. Other suitable oil-in-water emulsions include SAF (containing 10% Squalene, 0.4% Tween 80, 5% pluronic-blocked polymer L121, and thr-MDP, either microfluidized into a submicron emulsion or vortexed to generate a larger particle size emulsion) and Ribi$^T$ adjuvant system (RAS; containing 2% squalene, 0.2% Tween 80, and one or more bacterial cell wall components). Another class of preferred adjuvants is saponin adjuvants, such as Stimulon" (QS-21) or particles generated therefrom such as ISCOMs (immunostimulating complexes) and ISCOMATRIX. Other suitable adjuvants include incomplete or complete Freund's Adjuvant (IFA), cytokines, such as interleukins (IL-1, IL-2, and IL-12), macrophage colony stimulating factor (M-CSF), lysolecithin, tumor necrosis factor (TNF), and liposome polycation DNA particles. Such adjuvants are generally available from commercial sources.

In another embodiment of the present invention, the pharmaceutical composition further includes a delivery vehicle. Suitable delivery vehicles include, but are not limited to biodegradable microspheres, microparticles, nanoparticles, liposomes, collagen minipellets, and cochleates.

In one embodiment of this aspect of the invention, the pharmaceutical agent includes a mucosal delivery system. A preferred mucosal delivery system consists of attenuated *Salmonella* (e.g., *Salmonella typhimurium*) with a non-toxic fragment C of tetanus toxin (TetC) or glutathione S-transferase (GST). Methods of mucosal vaccination via oral administration of *S. typhimurium* are described in Goni et al., "Mucosal Vaccination Delays or Prevents Prion Infection via an Oral Route," *Neuroscience* 133:413-21 (2005), and Goni et al., "High Titers of Mucosal and Systemic Anti-PrP Antibodies Abrogate Oral Prion Infection in Mucosal-Vaccinated Mice," *Neuroscience* 153:679-686 (2008), which are hereby incorporated by reference in their entirety.

Another aspect of the present invention relates to a method of inducing an immune response against an amyloidogenic form of a protein or peptide in a subject. This method involves administering to the subject a polymerized product of the present invention under conditions effective to induce an immune response against the amyloidogenic form of the protein or peptide in the subject. In a preferred embodiment of this aspect of the present invention, a subject that would benefit from an immune response against an amyloidogenic form of a protein or peptide is selected prior to administering the polymerized product.

As used herein, an "amyloid protein", "amyloidogenic protein", and "amyloidogenic form of a protein" are used interchangeably to encompasses any insoluble fibrous protein/peptide aggregate that is deposited intra- or extracellularly within the body. Amyloidogenic protein/peptide deposition may be organ-specific (e.g., central nervous system, pancreas, etc.) or systemic. In accordance with this aspect of the invention, amyloidogenic proteins/peptides subject to deposition include beta protein precursor, prion and prion proteins, α-synuclein, tau, ABri precursor protein, ADan precursor protein, amylin, apolipoprotein AI, apolipoprotein AII, lyzozyme, cystatin C, gelsolin, protein, atrial natriuretic factor, calcitonin, keratoepithelin, lactoferrin, immunoglobulin light chains, transthyretin, A amyloidosis, β2-microglobulin, immunoglobulin heavy chains, fibrinogen alpha chains, prolactin, keratin, and medin. Amyloid deposition may occur as its own entity or as a result of another illness (e.g., multiple myeloma, chronic infection, or chronic inflammatory disease).

In accordance with this aspect of the present invention, an immune response is the development of a beneficial humoral (antibody mediated) and/or a cellular (mediated by antigen-specific T cells or their secretion products) response directed against the polymerized, non-fibrillogenic proteins or peptides of the polymerized product and cross-reactive with any amyloidogenic protein. Such a response is an active response induced by administration of the immunogenic polymerized protein and/or peptides and represents a therapeutic means for clearing or removing amyloid protein deposits from the body of the subject.

The presence of a humoral immunological response can be determined and monitored by testing a biological sample (e.g., blood, plasma, serum, urine, saliva feces, CSF or lymph fluid) from the subject for the presence of antibodies directed to the immunogenic component of the administered polymerized product. Methods for detecting antibodies in a biological sample are well known in the art, e.g., ELISA, Dot blots, SDS-PAGE gels or ELISPOT. The presence of a cell-mediated immunological response can be determined by proliferation assays (CD4+ T cells) or CTL (cytotoxic T lymphocyte) assays which are readily known in the art.

The present invention is further directed to a method of preventing and/or treating a condition mediated by an amyloidogenic protein or peptide in a subject. This method involves administering to the subject, a polymerized product of the present invention containing one or more polymers or co-polymers comprising an amyloid-beta (Aβ) peptide, an α-synuclein protein or peptide, a tau protein or peptide, a TAR DNA-binding protein 43 (TDP-43) protein or peptide, an amylin protein or peptide, a prion protein (PrP) or peptide or any combination thereof as described supra. The polymerized product is administered under conditions effective to treat the condition mediated by the amyloidogenic protein or peptide in the subject. In a preferred embodiment of this aspect of the present invention, a subject at risk of having or having a condition mediated by an amyloidogenic protein or peptide is selected prior to administering the polymerized product of the present invention.

Conditions or diseases associated with, or resulting from, the deposition of amyloidogenic proteins or peptides include, but are not limited to, Alzheimer's disease, diffuse Lewy body disease, Down's syndrome, fronto-temporal dementia, Parkinson's disease, hereditary cerebral hemorrhage with amyloidosis, kuru, Creutzfeldt-Jakob disease, Gerstmann-Straussler-Scheinker disease, fatal familial insomnia, British familial dementia, Danish familial dementia, familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever, dialysis-associated amyloidosis, systemic amyloidosis, and familial systemic amyloidosis. In accordance with this aspect of the present invention, administration of the polymerized product is effective to stimulate an immune response in the subject that is effective at reducing and/or clearing the amyloidogenic protein that is causing or exacerbating the aforementioned disease conditions.

A second aspect of the present invention is directed to an isolated antibody or binding portion thereof having antigenic specificity for an epitope a non-amyloidogenic, non-fibrillogenic polymerized product of the present invention. As described infra, the polymerized product of the present invention comprises two or more protein or peptide units, each unit independently selected from the group consisting of an amyloid-beta (Aβ) peptide, an α-synuclein protein or peptide, a tau protein or peptide, a TAR DNA-binding protein 43 (TDP-43) protein or peptide, an amylin protein or peptide, a prion protein (PrP) protein or peptide, and any combination thereof.

As used herein, "epitope" refers to an antigenic determinant of the one or more polymerized proteins or peptides of the present invention that is recognized by the isolated antibody. The epitope recognized by the antibody of the present invention may be a linear epitope, i.e. the primary structure of the amino acid sequence of the target proteins or peptides. Preferably, the linear epitope recognized by the isolated antibody of the present invention does not have amino acid sequence homology to a non-amyloid protein. Alternatively, the epitope recognized by the isolated antibody of the present invention is a non-linear or conformational epitope, i.e. the tertiary or quatemary structure of a polymerized protein or peptide. In one embodiment of the present invention, the non-linear or conformational epitope recognized by the isolated antibody of the present invention is a conformational epitope that is common to or shared with one or more, or all, amyloidogenic proteins. Accordingly, the isolated antibody of the present invention has antigenic specificity for a shared conformational epitope common to all amyloidogenic proteins known in the art.

An isolated antibody of the present invention encompasses any immunoglobulin molecule that specifically binds to an epitope of a polymerized product of the present invention. Preferably, the antibody of the present invention binds specifically to an epitope that is shared by a polymerized product of the present invention and one or more amyloidogenic proteins. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies, and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli.*" *Proc Natl Acad Sci USA* 85:5879-5883 (1988); Bird et al, "Single-Chain Antigen-Binding Proteins," *Science* 242:423-426 (1988)).

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the invention or the synthesis of an amino acid specifying the antibody, where the DNA or amino acid sequence has been obtained using synthetic DNA or amino acid sequence technology which is available and well known in the art.

Methods for monoclonal antibody production may be carried out using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., a polymerized protein or peptide product of the present invention) either in vivo or in vitro. Exemplary polymerized products comprising one or more Aβ peptides, α-synuclein proteins or peptides, tau proteins or peptides, TDP-43 proteins or peptides, amylin proteins or peptides, and a prion proteins or peptides are described supra.

The antibody-secreting lymphocytes are fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which may be murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, and monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348: 552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences.

An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

The monoclonal Aβ of the present invention can also be a human monoclonal Aβ. A human antibody is an antibody produced by a human or an antibody having an amino acid sequence corresponding to an antibody produced by a human. Human antibodies can be produced using various techniques known in the art. Immortalized human B lymphocytes immunized in vitro or isolated from an immunized individual that produce an antibody directed against a target antigen can be generated (See e.g., Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the human antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227:381-8 (1992); Marks et al., "By-passing Immunization. Human Antibodies from V-gene Libraries Displayed on Phage," *J Mol Biol* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known in the art. Typically, such antibodies are raised by administering the polymerized product of the present invention subcutaneously to rabbits (e.g., New Zealand white rabbits), goats, sheep, swine, or donkeys which have been bled to obtain pre-immune serum. The polymerized product can be injected in combination with an adjuvant. The rabbits are bled approximately every two weeks after the first injection and periodically boosted with the same antigen three times every six weeks. Polyclonal antibodies are recovered from the serum by affinity chromatography using the corresponding polymerized product to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

As noted above, in addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Also suitable for use in the present invention are antibody fragments engineered to bind to intracellular proteins, i.e. intrabodies. Although amyloid protein deposits are generally extracellular, intracellular accumulation of certain amyloid proteins (e.g., Aβ1-42) have been observed (D'Andrea et al., "Targeting Amyloid Beta: Targeting Intracellular A042 for Alzheimer's Disease Drug Discover," *Drug Development Research* 56:194-200 (2002); Knobloch et al., "Intracellular Abeta and Cognitive Deficits Precede beta-Amyloid Deposition in arcAbeta Mice," *Neurobiol Aging* 28(9): 1297-306 (2007), which are hereby incorporated by reference in their entirety). Accordingly, an intrabody can be used to bind selectively to an epitope of an amyloid protein within a cell. In a preferred embodiment, the intrabody recognizes an epitope of the Aβ1-42 oligomer accumulating within the perikaryon of affected neurons (e.g., pyramidal neurons) in AD.

Intrabodies are generally obtained by selecting a single variable domain from variable regions of an antibody having two variable domains (i.e., a heterodimer of a heavy chain variable domain and a light chain variable domain). Single chain Fv fragments, Fab fragments, ScFv-Ck fusion proteins, single chain diabodies, $V_H$—$C_H$1 fragments, and even whole IgG molecules are suitable formats for intrabody development (Kontermann R. E., "Intrabodies as Therapeutic Agents," *Methods* 34:163-70 (2004), which is here by incorporated by reference in its entirety).

Intrabodies having antigen specificity for a conformational epitope of an amyloidogenic protein can be obtained from phage display, yeast surface display, or ribosome surface display. Methods for producing libraries of intrabodies and isolating intrabodies of interest are further described in U.S. Published Patent Application No. 20030104402 to Zauderer and U.S. Published Patent Application No. 20050276800 to Rabbitts, which are hereby incorporated by reference in their entirety. Methods for improving the stability and affinity binding characteristics of intrabodies are described in WO2008070363 to Zhenping; Contreras-Martinez et al., "Intracellular Ribosome Display via SecM Translation Arrest as a Selection for Antibodies with Enhanced Cytosolic Stability," *J Mol Biol* 372(2):513-24 (2007), which are hereby incorporated by reference in their entirety.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J Mol Biol* 284:1141-1151 (1998); Koide et al., "Probing Protein Conformational Changes in Living Cells by Using Designer Binding Proteins: Application to the Estrogen Receptor," *Proc Natl Acad Sci USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol* 15(8):772-777 (1997), which is hereby incorporated by reference in its entirety).

The present invention is further directed to a pharmaceutical composition containing the isolated antibody of the present invention as described supra. In a preferred embodiment, the isolated antibody recognizes and binds to a shared conformational epitope common to one or more amyloid proteins. The pharmaceutical composition of the present invention may contain an antibody mixture where all antibodies recognize the same conformational epitope. Alternatively, the pharmaceutical composition may contain an antibody mixture where one or more antibodies recognize one or more different conformational epitopes of amyloid proteins. The pharmaceutical composition of the present invention further contains a pharmaceutically acceptable carrier or other pharmaceutically acceptable components as described supra.

Another aspect of the present invention relates to a method of treating a condition mediated by an amyloidogenic protein in a subject. This method involves administering to the subject an antibody of the present invention, where the antibody has antigen specificity for an epitope of a non-amyloidogenic, non-fibrillogenic polymerized product, wherein the polymerized product comprises two or more protein and/or peptide units, each unit independently selected from the group consisting of an amyloid-beta (Aβ) peptide, an α-synuclein protein or peptide, a tau protein or peptide, a TAR DNA-binding protein 43 (TDP-43) protein or peptide, an amylin protein or peptide, a prion protein (PrP) protein or peptide, and any combination thereof. Preferably the antibody has antigen specificity for a shared conformational epitope that is common to one or more amyloidogenic proteins. The antibody or a pharmaceutical composition containing the antibody is administered in an amount effective to treat the condition involving the amyloidogenic protein in the subject. In accordance with this aspect of the invention, the antibody or pharmaceutical composition containing the antibody is administered in an amount effective to generate passive immunity in the subject against one or more amyloidogenic proteins, thereby facilitating the clearance of amyloid deposits from the subject.

Conditions mediated by an amyloidogenic protein that are amenable to treatment in accordance with this aspect of the present invention are described supra.

In a preferred embodiment of this aspect of the present invention, a subject having a condition or at risk of developing a condition mediated by an amyloidogenic protein is selected prior to administration of the antibody of the present invention. Subjects amenable to treatment in accordance with the methods of the present invention include individuals at risk of developing an amyloid related disease but not showing symptoms, as well as subjects showing symptoms at the time of therapeutic intervention (i.e. antibody administration). Diseases subject to treatment include any disease associated with or caused by an amyloidogenic protein as described supra. The pharmaceutical compositions of the present invention contain polymerized products that are not endogenous to the body, or antibodies specific for only pathological protein conformations. Therefore, the risk of inducing an autoimmune response is avoided and prophylactic treatment using these pharmaceutical compositions of the present invention is particularly suitable.

In the case of Alzheimer's disease, for example, virtually anyone is at risk of suffering from Alzheimer's disease if he or she lives long enough. Therefore, the compositions of the present invention can be administered prophylactically to the general population without the need for any assessment of the risk of the subject patient. However, the present methods and compositions are especially suitable for prophylactic treatment of individuals who have a known genetic risk of Alzheimer's disease or other condition related to an amyloidogenic protein. Genetic markers associated with a risk of Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and mutations in ApoE4, family history of AD, hypercholesterolemia, or atherosclerosis.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody, or activated T-cell or B-cell responses to the therapeutic agent (e.g., polymerized product) over time. If the response falls, a booster dosage is indicated. In the case of potential Down's syndrome patients, treatment can begin antenatally by administering the therapeutic agent to the mother or shortly after birth.

In prophylactic applications, the pharmaceutical compositions of the present invention are administered to a patient susceptible to, or otherwise at risk of, a particular disease in an amount sufficient to eliminate or reduce the risk or delay the onset of the disease. In therapeutic applications, pharmaceutical compositions are administered to a patient suspected of, or already suffering from an amyloidogenic disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the subject is a human, but in some diseases, such as prion protein related diseases, the subject can be a nonhuman mammal, such as a bovine. Other non-human mammals amenable to treatment in accordance with the methods of the present invention include primates, dogs, cats, rodents (e.g., mouse, rat, guinea pig), horses, deer, cervids, cattle and cows, sheep, and pigs. Treatment dosages need to be titrated to optimize safety and efficacy, and could involve oral treatment.

When treatment of a subject involves the administration of a polymerized product of the present invention containing one or more polymerized or copolymerized Aβ, α-synuclein, tau, TDP-43, amylin, and/or PrP protein or peptide immunogens, the appropriate dosage will depend on whether adjuvant is co-administered, with higher dosages being required in the absence of adjuvant. The amount of an immunogen for administration sometimes varies from 1 μg-500 μg per patient and more usually from 5-500 μg per injection for human administration. Occasionally, a higher dose of 1-2 mg per injection is used. Typically about 10, 20, 50 or 100 μg is used for each human injection. The timing of injections can vary significantly from once a day, to once a week, to once a month, to once a year, to once a decade. Generally an effective dosage can be monitored by obtaining a fluid sample from the patient, generally a blood serum sample, and determining the titer of antibody developed against the immunogen, using methods well known in the art and readily adaptable to the specific antigen to be measured. Ideally, a sample is taken prior to initial dosing and subsequent samples are taken and titered after each immunization. Generally, a dose or dosing schedule which provides a detectable titer at least four times greater than control or "background" levels at a serum dilution of 1:100 is desirable, where background is defined relative to a control serum or relative to a plate background in ELISA assays.

On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with a composition comprising an antibody of the present invention, the dosage ranges from about 0.0001 to 100 mg/kg, and more usually 0.01 to 5 mg/kg of the host body weight. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to polymerized proteins or peptide in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and non-human antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Compositions of the present invention, i.e., polymerized products and antibodies, can be administered by parenteral, topical, intravenous, oral, subcutaneous, intraperitoneal, intranasal or intramuscular means for prophylactic and/or therapeutic treatment. The most typical route of administration for compositions formulated to induce an immune response is subcutaneous although others can be equally effective. The next most common is intramuscular injection. This type of injection is most typically performed in the arm or leg muscles. Intravenous injections as well as intraperitoneal injections, intra-arterial, intracranial, or intradermal injections are also effective in generating an immune response. In some methods, agents such as antibodies are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

The pharmaceutical agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the compositions of the present invention may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Another aspect of the present invention relates to a method of diagnosing an amyloid disease in a subject. This method involves detecting, in the subject, the presence of an amyloidogenic proteins or peptides using a diagnostic reagent, where the diagnostic reagent is an antibody, or active binding fragment thereof, of the present invention. As described supra, the antibody has antigenic specificity for a conformational epitope of an amyloidogenic form of a protein. Preferably the conformational epitope recognized by the antibody is shared with one or more other amyloidogenic protein or peptides. The diagnosis of the amyloid disease is based on the detection of an amyloidogenic protein or peptide in the subject.

Detecting the presence of amyloidogenic deposits in a subject using the diagnostic reagent can be achieved by obtaining a biological sample from the subject (e.g., blood, urine, cerebral spinal fluid), contacting the biological sample with the diagnostic antibody reagent, and detecting binding of the diagnostic antibody reagent to an amyloidogenic protein in the sample from the subject. Assays for carrying out the detection of an amyloid protein in a biological sample using a diagnostic antibody are well known in the art and include, without limitation, ELISA, immunohistochemistry, western blot.

Alternatively, detecting the presence of amyloid deposits in a subject using diagnostic antibody reagent of the present invention can be achieved using in vivo imaging techniques. In vivo imaging involves administering to the subject the diagnostic antibody having antigenic specificity for a conformational epitope of a polymerized product containing two or more protein and/or peptide units where each unit is independently selected from the group consisting of Aβ, α-synuclein, tau, TDP-43, amylin, and/or PrP proteins or peptides, and detecting the binding of the diagnostic agent to the amyloidogenic protein in vivo. As described supra, preferred antibodies bind to a conformational epitope of an amyloidogenic form of a protein or peptide without binding to the non-amyloidogenic proteins and without binding to the non-pathological forms of the amyloidogenic proteins.

Diagnostic antibodies or similar reagents can be administered by intravenous injection into the body of the patient, or directly into the brain by intracranial injection or by drilling a hole through the skull. The dosage of antibody should be within the same ranges as for treatment methods. Typically, the antibody is labeled, although in some methods, the primary antibody with affinity for the conformational epitope of an amyloid protein is unlabelled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled amyloid protein deposits in a sample from the subject or in the subject, to corresponding baseline values. An appropriate baseline value can be the average level of amyloid protein deposition in a population of undiseased individuals. Alternatively, an appropriate baseline value may be the level of amyloid protein deposition in the same subject determined at an earlier time.

The diagnostic methods described above can also be used to monitor a subject's response to therapy. In this embodiment, detection of amyloid deposits in the subject is determined prior to the commencement of treatment. The level of amyloid deposition in the subject at this timepoint is used as a baseline value. At various times during the course of treatment the detection of amyloid deposits can be repeated, and the measured values thereafter compared with the baseline values. A decrease in values relative to baseline signals a positive response to treatment.

The present invention is further directed to a kit for performing the above described diagnostic and monitoring methods. Typically, such kits contain a diagnostic antibody reagent, preferably the antibody of the present invention that has antigenic specificity for a polymerized Aβ, α-synuclein, tau, TDP-43, amylin, and/or PrP protein or peptide product. The kit can also include a detectable label. The diagnostic antibody itself may contain the detectable label (e.g., fluorescent molecule, biotin, etc.) which is directly detectable or detectable via a secondary reaction (e.g., reaction with strepavidin). Alternatively, a second reagent containing the detectable label may be utilized, where the second reagent has binding specificity for the primary antibody. In a diagnostic kit suitable for measuring amyloid in a biological sample, the antibodies of the kit may be supplied prebound to a solid phase, such as to the wells of a microtiter dish.

Diagnostic kits of the present invention also include kits that are useful for detecting antibody production in a subject following administration of a polymerized protein or peptide of the present invention. Typically, such kits include a reagent that contains the antigenic epitope of the antibodies generated by the subject in a polymerized product as described supra. The kit also includes a detectable label. In a preferred embodiment, the label is typically in the form of labeled anti-idiotypic antibodies. The antigenic epitope reagents of the kit can be supplied prebound to a solid phase, such as to the wells of a microtiter dish.

EXAMPLES

The following examples are provided to illustrate embodiments of the present invention but they are by no means intended to limit its scope.

Materials and Methods for Examples 1-4

Peptide Synthesis:

The 42 amino acid AB peptide (SEQ ID NO: 1), the ABri peptide (Cys-Ser-Arg-Thr-Val-Lys-Lys-Asn-Ile-Ile-Glu-Glu-Asn) (SEQ ID NO:8), and Aβ1-30$K_{18}K_{19}$ (daefrhdsgy evhhqklkkf aedvgsnkga) (SEQ ID NO: 12) were synthesized on an ABI 430A peptide synthesizer (AME Bioscience, Chicago, Ill.) at the Keck peptide synthesis facility at Yale University, CT, using a Vydac C18 preparative column, 2.5×30 cm (Vydac Separations, Hesperia, Calif.). Standard protocols for tBOC (tert-butyloxycarbonyl) chemistry were used. The peptides were subsequently cleaved from the resins using hydrofluoric acid and purified by high-pressure liquid chromatography (HPLC) on a Vydac C18 preparative column using linear gradients from 0-70% of acetonitrile in 0.1% trifluoroacetic acid. Mass spectroscopy of the lyophilized end-product was used to verify the expected molecular weight.

Peptide Polymerization and Assessment of Conformation.

In order to make the peptides immunogenic and to potentially ensure a conformation specific immune response, the peptides were first subjected to controlled polymerization using the following protocol. Peptides were dissolved at 3 mg/ml, in 100 mM borate buffer saline (BBS), pH 7.4. Fresh 1% glutaraldehyde in BBS was prepared and added to the peptide to a final 5 mM glutaraldehyde concentration and incubated in an Eppendorf block at 800 rpm at 56° C. for 16 hrs. The solution was then quenched with 0.5 M glycine to make the solution 100 mM in glycine. After five minutes the solution was diluted 1:3 with BBS, dialyzed against 2 mM BBS overnight at 4° C., aliquoted, and lyophilized.

For electron microscopic studies of the polymerized Aβ peptide, the original and polymerized peptides were incubated at 1 mg/ml in phosphate buffered saline, pH 7.4. The sample (3 µl) was put onto a carbon coated 400 mesh Cu/Rh grid (Ted Pella Inc., Redding, Calif.) and stained with 1% uranyl acetate in distilled water (Polysciences, Inc, Warrington, Pa.). Stained grids were examined under a Philips CM-12 electron microscope (FEI; Eindhoven, The Netherlands) and photographed with a (1 k×1 k) digital camera (Gatan, Inc., Pleasanton, Calif.).

Immunization of Mice.

Animal studies were approved by the NYU School of Medicine Institutional Animal Care and Use Committee and were consistent with the recommendations of the American Veterinary Association. Two transgenic (Tg) mouse models were used in these experiments. The first model, the 3×Tg model, develops both plaque and tangle pathology (Oddo et al., "Triple-Transgenic Model of Alzheimer's Disease with Plaques and Tangles: Intracellular Abeta and Synaptic Dysfunction," *Neuron* 39:409-21 (2003), which is hereby incorporated by reference in its entirety). The second model, the TgSwDI model, develops extensive congophilic angiopathy (CAA) (Davis et al., "Early-Onset and Robust Cerebral Microvascular Accumulation of Amyloid Beta-Protein in Transgenic Mice Expressing Low Levels of a Vasculotropic Dutch/Iowa Mutant Form of Amyloid Beta-Protein Precursor," *J. Biol. Chem.* 279:20296-306 (2004), which is hereby incorporated by reference in its entirety). Starting at the age of 3 months mice were immunized 4 times biweekly, subcutaneously with 50 µg/animal of polymerized peptide in sterile saline:Alum 9:1, and thereafter 4 times bimonthly with 25 µg/animal until the 12 month. At the age of 15-16 months mice were subject to locomotor and cognitive behavioral testing (radial arm maze), followed by histological and biochemical analysis. Animals were bled from the caudal vein prior to inoculation (T0), after the $6^{th}$ inoculation (T6) and at the time of sacrifice (TF). The blood was collected in heparinized tubes and plasma separated and stored at −80° C.

Locomotor and Cognitive Behavioral Testing.

Locomotor Activity:

A Hamilton-Kinder Smart-frame Photobeam System was used to make a computerized recording of animal activity over a designated period of time. Exploratory locomotor activity is recorded in a circular open field activity chamber measuring (70×70 cm). A video camera mounted above the chamber automatically recorded horizontal movements in the open field in each dimension (i.e., x, y, and two z planes). Total distance was measured in centimeters (cm) traveled and is defined as sequential movement interruptions of the animal measured relative to the background. The duration of the behavior was timed for 15 min. Results were reported based on distance traveled (cm), mean resting time, and maximum velocity of the animal.

Radial Arm Maze:

Prior to testing, the mice were adapted to the room with lights on for 15 min. Spatial learning was evaluated using an eight-arm radial maze with a water well at the end of each arm. Clear Plexiglas guillotine doors, operated by a remote pulley system, controlled access to the arms from a central area from which the animals entered and exited the apparatus. After 3-4 days of adaptation, water-restricted mice (2 hours daily access to water) were given one training session per day for ten consecutive days. For each session, all arms were baited with saccharine flavored water, and animals were permitted to enter all arms until the eight rewards had been consumed. The number of errors (entries to previously visited arms) and time to complete each session were recorded.

Antibody Levels.

Antibody levels were determined in duplicate on 1:100 dilutions of plasma using ELISA as described previously (Goni et al., "Mucosal Vaccination Delays or Prevents Prion Infection Via an Oral Route," Neurosci. 133:413-421 (2005); Asuni et al., "Aβ Derivative Vaccination in Alum Adjuvant Prevents Amyloid Deposition and Does Not Cause Brain Microhemorrhages in Alzheimer's Model Mice," Eur. J. Neurosci. 24:2530-2542 (2006), which are hereby incorporated by reference in their entirety), in which 5 µg/plate Aβ1-40, Aβ1-42, Aβ1-30KK, or pABri was coated onto Immulon 2HB 96 well microtiter wells (Thermo, Waltham, Mass.). The bound antibodies were detected by a horseradish peroxidase labeled goat anti-mouse IgG (Amersham Biosciences, Piscataway, N.J.) or a peroxidase conjugated goat anti-mouse IgM (Sigma; A8786). Tetramethyl benzidine (TMB; Pierce, Rockford, Ill.) was the color developing substrate and the readings were done at 450 nm.

Histology.

Mice were anesthetized with sodium pentobarbital (150 mg/kg, i.p.), perfused transaortically with phosphate buffer, and the brains processed as described previously (Asuni et al., "Aβ Derivative Vaccination in Alum Adjuvant Prevents Amyloid Deposition and Does Not Cause Brain Microhemorrhages in Alzheimer's Model Mice," Eur. J. Neurosci. 24:2530-2542 (2006); Sigurdsson et al., "An Attenuated Immune Response is Sufficient to Enhance Cognition in an Alzheimer's Disease Mouse Model Immunized With Amyloid-β Derivatives," J. Neurosci. 24:6277-6282 (2004), which are hereby incorporated by reference in their entirety). Serial coronal sections (40 µm) were stained with a mixture of 4G8/6E10, monoclonal antibodies that recognizes Aβ and stains both pre-amyloid and Aβ plaques (Sadowski et al., "Blocking the Apolipoproteine/Amyloid 3 Interaction Reduces the Parenchymal and Vascular Amyloid-β Deposition and Prevents Memory Deficit in AD Transgenic Mice," Proc. Natl. Acad. Sci. (USA) 103:18787-18792 (2006); Scholtzova et al., "Induction of Toll-Like Receptor 9 Signaling as a Method for Ameliorating Alzheimer's Disease Related Pathology," J. Neurosci. 29:1846-1854 (2009), which are hereby incorporated by reference in their entirety). Immunostaining was performed as described previously (Sadowski et al., "Blocking the Apolipoproteine/Amyloid β Interaction Reduces the Parenchymal and Vascular Amyloid-β Deposition and Prevents Memory Deficit in AD Transgenic Mice," Proc. Natl. Acad. Sci. (USA) 103:18787-18792 (2006); Scholtzova et al., "Induction of Toll-Like Receptor 9 Signaling as a Method for Ameliorating Alzheimer's Disease Related Pathology," J. Neurosci. 29:1846-1854 (2009), which are hereby incorporated by reference in their entirety). All procedures were performed by an individual blinded to the experimental conditions of the study. The Aβ burden is defined as the percentage of area in the measurement field occupied by reaction product.

Example 1—Locomotor and Cognitive Testing

Figure 1B:
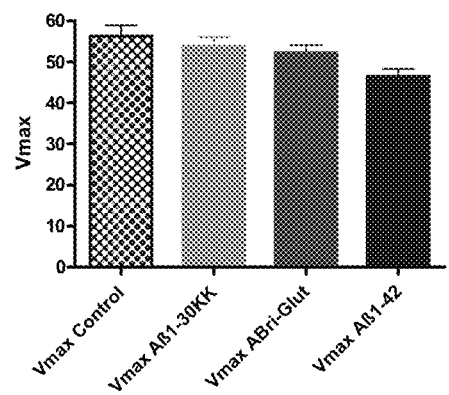
Figure 1C:
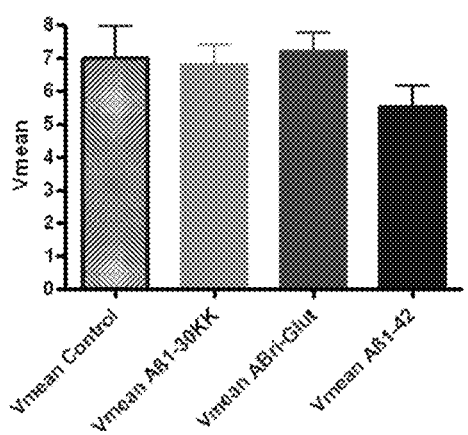
Figure 1D:
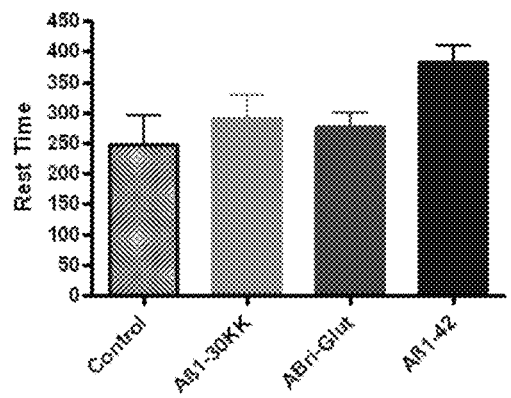
Figure 2A:
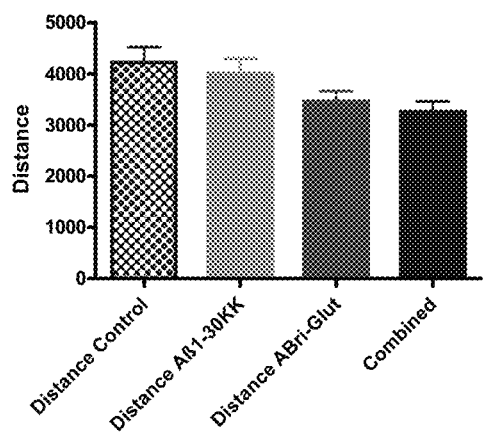
FIGS. 2A-2D show the results of locomotor activity testing in Tg3x transgenic control mice and Tg mice vaccinated with synthetic polymerized Aβ peptide (Aβ1-30$K_{18}K_{19}$), polymerized ABri peptide (ABri-Glut), or the combination of Aβ1-30 $K_{18}K_{19}$ and ABri polymerized peptides. No significant differences between the groups were noted in distance traveled (FIG. 2A), maximum velocity (Vmax) (FIG. 2B), mean velocity (Vmean) (FIG. 2C), or in resting time (FIG. 2D).
Figure 2B:
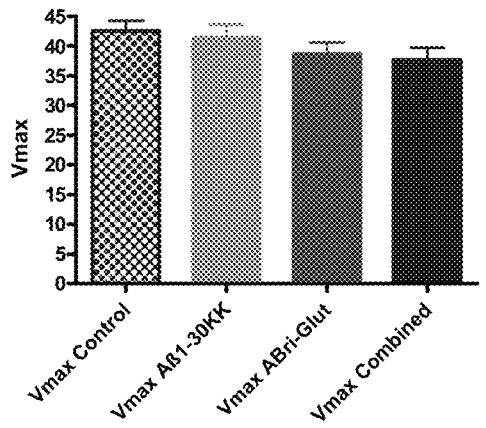
Figure 2C:
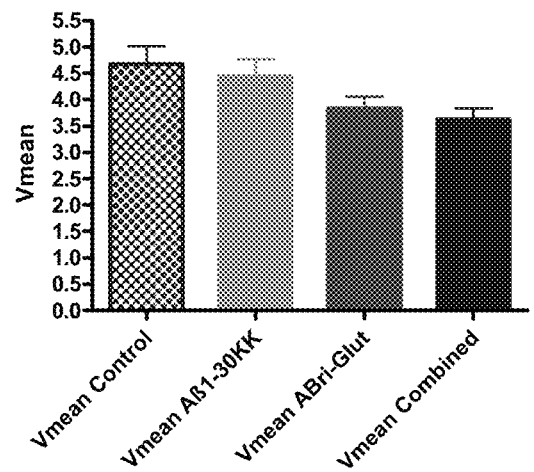
Figure 2D:
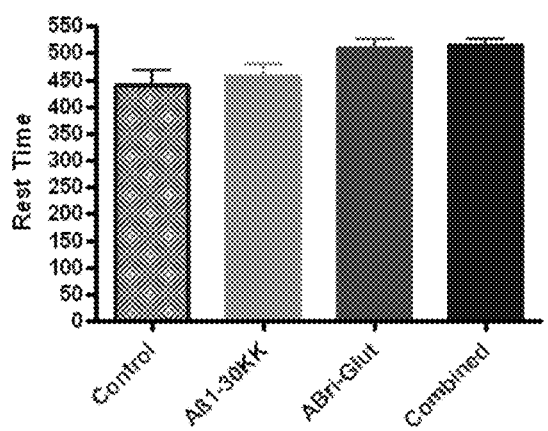

In order to verify that cognitive testing was not confounded by differences in sensorimotor abilities in the polymerized peptide vaccinated versus control Tg3x and SwDI transgenic mice, locomotor testing was conducted first. There was no significant differences between SwDI Tg control mice and SwDI Tg mice vaccinated with polymerized Aβ1-30$_{18}$K$_{19}$K, polymerized ABri peptide (ABri-Glut), or polymerized Aβ1-42 peptide in distance traveled (FIG. 1A) or mean velocity (Vmean) (FIG. 1C). Aβ1-42 vaccinated Tg mice exhibited slower maximum velocity (Vmax) (FIG. 1B) (p=0.0234 post-hoc only; Aβ1-42 versus control p<0.05) and longer resting time (FIG. 1D) (p=0.0311 post-hoc only; Aβ1-42 versus control p<0.05) compared to controls. No significant differences between the Aβ1-30$_{18}$K$_{19}$K and ABri treated Tg animals versus controls in these parameters were observed (FIGS. 1B and 1D). There was no significant difference between Tg3x control mice and Tg3x mice vaccinated with a synthetic polymerized Aβ1-30K$_{18}$K$_{19}$, polymerized ABri peptide (ABri-Glut), or the combination of Aβ1-30 K$_{18}$K$_{19}$ and ABri polymerized peptides in distance traveled (FIG. 2A), maximum velocity (Vmax) (FIG. 2B), mean velocity (Vmean) (FIG. 2C), or in resting time (FIG. 2D).

Figure 3A:
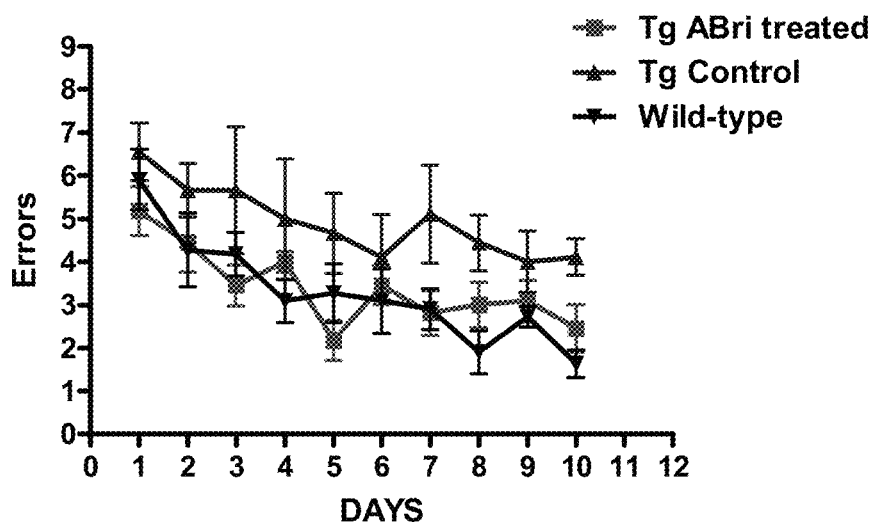
FIGS. 3A-3C illustrate the effects of polymerized peptide vaccination on behavioral improvement in 3×Tg and SwDI transgenic animal models of amyloidogenic disease.
Figure 3B:
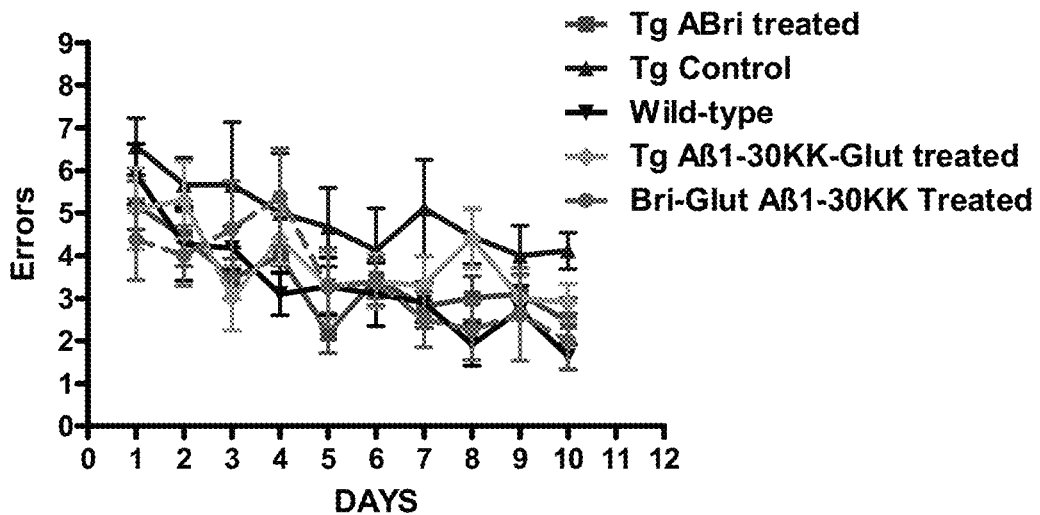

Radial arm maze cognitive testing showed there were significant differences between the untreated control Tg3x mice (Tg control) versus Aβri treated Tg mice and wild-type controls (FIG. 3A). There was no difference between the wild-type controls and the ABri vaccinated Tg3x mice. There was also a significant difference between the untreated control Tg3x mice (Tg control) versus animals vaccinated with the polymerized Aβ1-30K$_{18}$K$_{19}$ peptide and animals vaccinated with the combination of polymerized ABri and Aβ1-30K$_{18}$K$_{19}$ peptides (FIG. 3B).

Figure 3C:
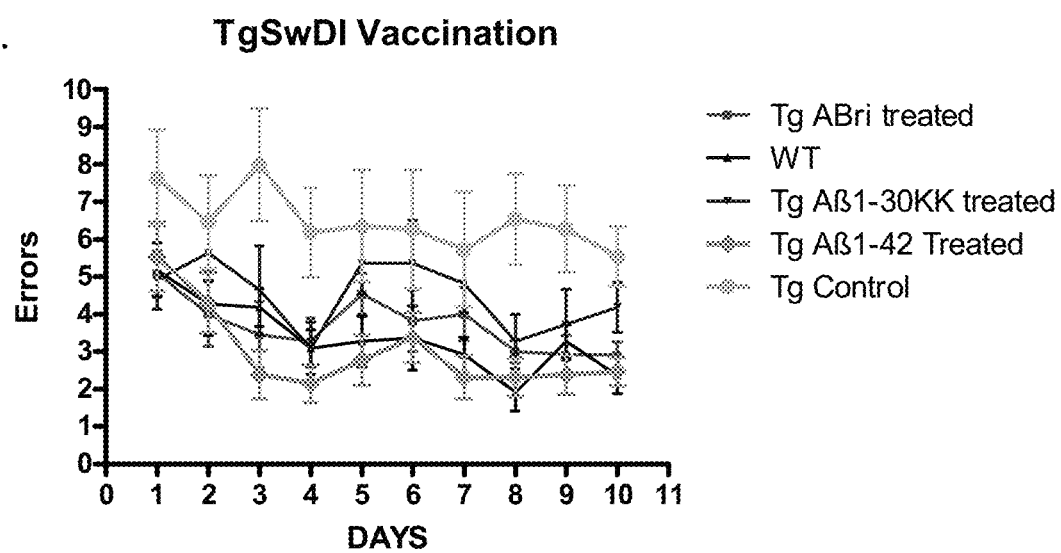

Radial arm maze cognitive testing in the SwDI Tg mice showed there were significant differences between the untreated control SwDI Tg mice (Tg Control) versus the polymerized Aβ1-42, Aβ1-30K$_{18}$K$_{19}$, and Aβri treated Tg mice and wild-type controls (FIG. 3C). There was no difference between the wild-type controls and the vaccinated SwDI Tg mice.

Example 2—Antibody Titers

Figure 4A:
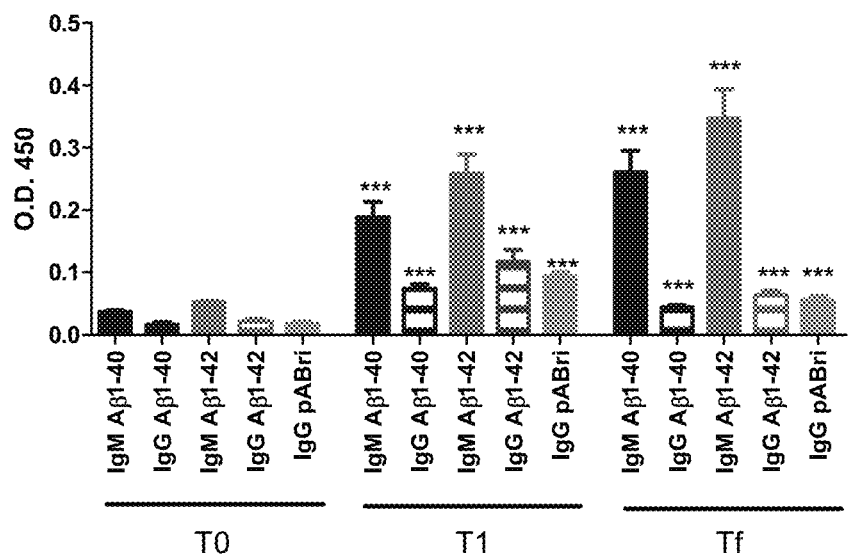
FIGS. 4A-4C are bar graphs showing IgM and IgG antibody levels raised in TgSwDI mice vaccinated with polymerized ABri peptide (pABri) (FIG. 4A), polymerized Aβ1-30$K_{18}K_{19}$ (FIG. 4B), and polymerized Aβ1-42 peptide (FIG. 4C). Antibody titers against Aβ1-40, Aβ1-42, pABri, and a mutant Aβ1-30KK were measured in vaccinated mice prior to the first inoculation (T0), after the 6th inoculation (T1) and at the time of sacrifice (TF). (*p<0.0001, p<0.01, *p>0.05 versus T0).
Figure 4B:
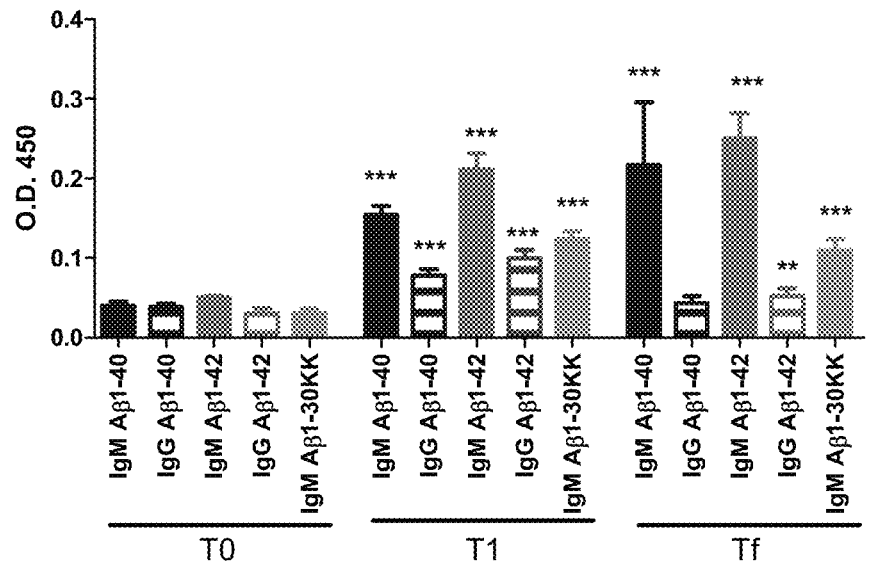
Figure 4C:
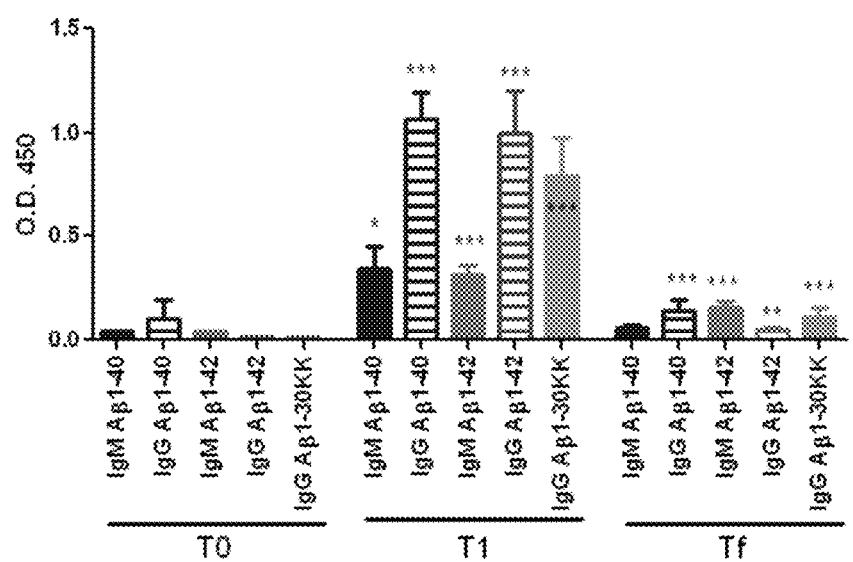

In TgSwDI mice vaccinated with polymerized ABri, significant IgG and IgM titers were noted against Aβ31-40, Aβ1-42, and polymerized ABri at T1 and Tf (FIG. 4A). In TgSwDI mice vaccinated with polymerized Aβ1-30K$_{18}$K$_{19}$, significant IgG and IgM titers were noted against Aβ31-40, Aβ1-42, and Aβ1-30K$_{18}$K$_{19}$ at T1 (FIG. 4B). Significant IgM titers against Aβ1-40, Aβ1-42, and Aβ1-30 K$_{18}$K$_{19}$, and significant IgG titers against Aβ1-42 were observed at Tf (FIG. 4B). In TgSwDI mice vaccinated with polymerized Aβ1-42, significant IgG and IgM titers were also noted against Aβ1-40, Aβ1-42, and Aβ1-30K$_{18}$K$_{19}$ at T1, and to a lesser extent at Tf (see FIG. 4C).

Figure 5A:
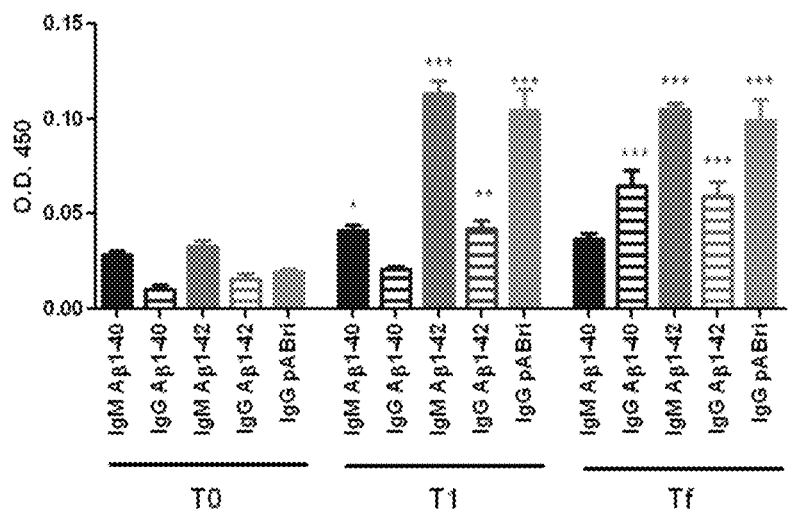
FIGS. 5A-5D are bar graphs showing IgM and IgG antibody levels raised in 3×Tg mice vaccinated with polymerized ABri peptide (FIG. 5A), polymerized Aβ1-30$K_{18}K_{19}$ (FIG. 5B), the combination of polymerized peptides (FIG. 5C), and vehicle (FIG. 5D). Antibody titers against Aβ1-40, Aβ1-42, pABri, and a mutant Aβ1-30KK were measured in vaccinated mice prior to the first inoculation (T0), after the 6th inoculation (T1), and at the time of sacrifice (TF). (*p<0.0001, p<0.01, *p>0.05 versus T0).
Figure 5B:
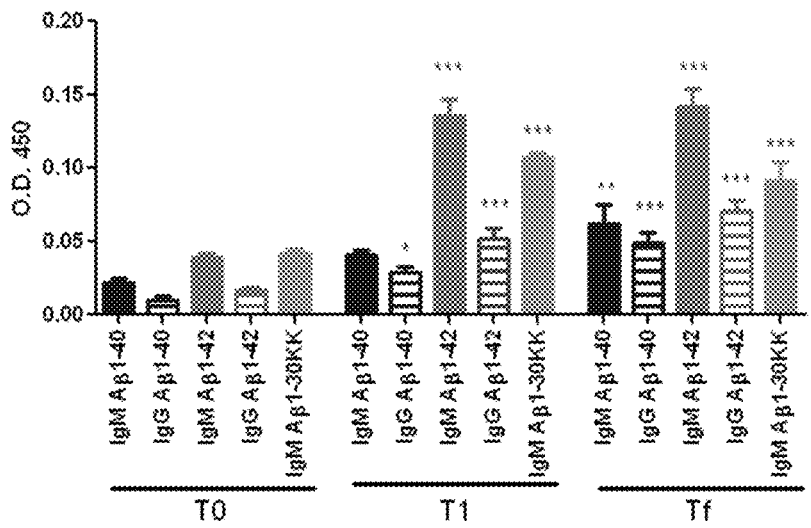
Figure 5C:
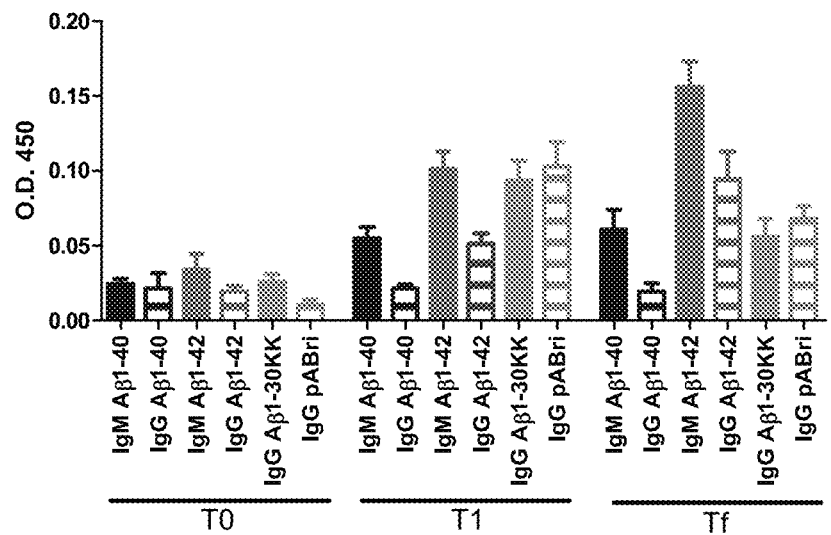
Figure 5D:
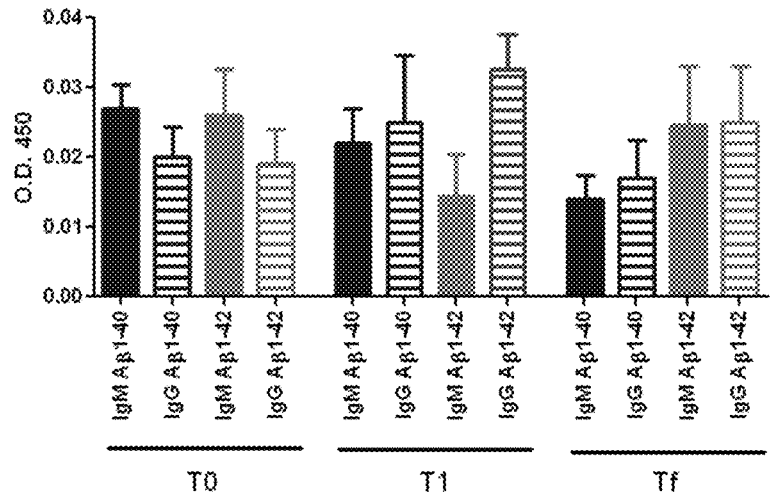

In Tg3x mice vaccinated with polymerized ABri, significant IgG and IgM titers were noted against Aβ1-42 and polymerized ABri at T1 and Tf (FIG. 5A). Significant IgM titers against Aβ1-40 were observed at T1, and significant IgG titers against Aβ1-40 were observed at Tf in these animals. In the polymerized Aβ1-30K$_{18}$K$_{19}$ vaccinated Tg3x mice, significant IgG and IgM titers were noted against Aβ1-42 and Aβ1-30K$_{18}$K$_{19}$ at T1 and Tf, and significant IgM and IgG antibodies against Aβ1-40 were observed at Tf (FIG. 5B). In Tg3x animals vaccinated with the combination of polymerized Aβ1-30K$_{18}$K$_{19}$ and ABri, significant IgG and IgM titers were also noted against Aβ1-42, AI-30K$_{18}$K$_{19f}$, and ABri at T1 and Tf (see FIG. 5C). FIG. 5D shows that IgG and IgM antibody titer against Aβ1-40 and Aβ1-42 does not differ significantly in vehicle treated transgenic 3×Tg animals.

Example 3—Amyloid Burden

Figures 6A, 6B, 6C:
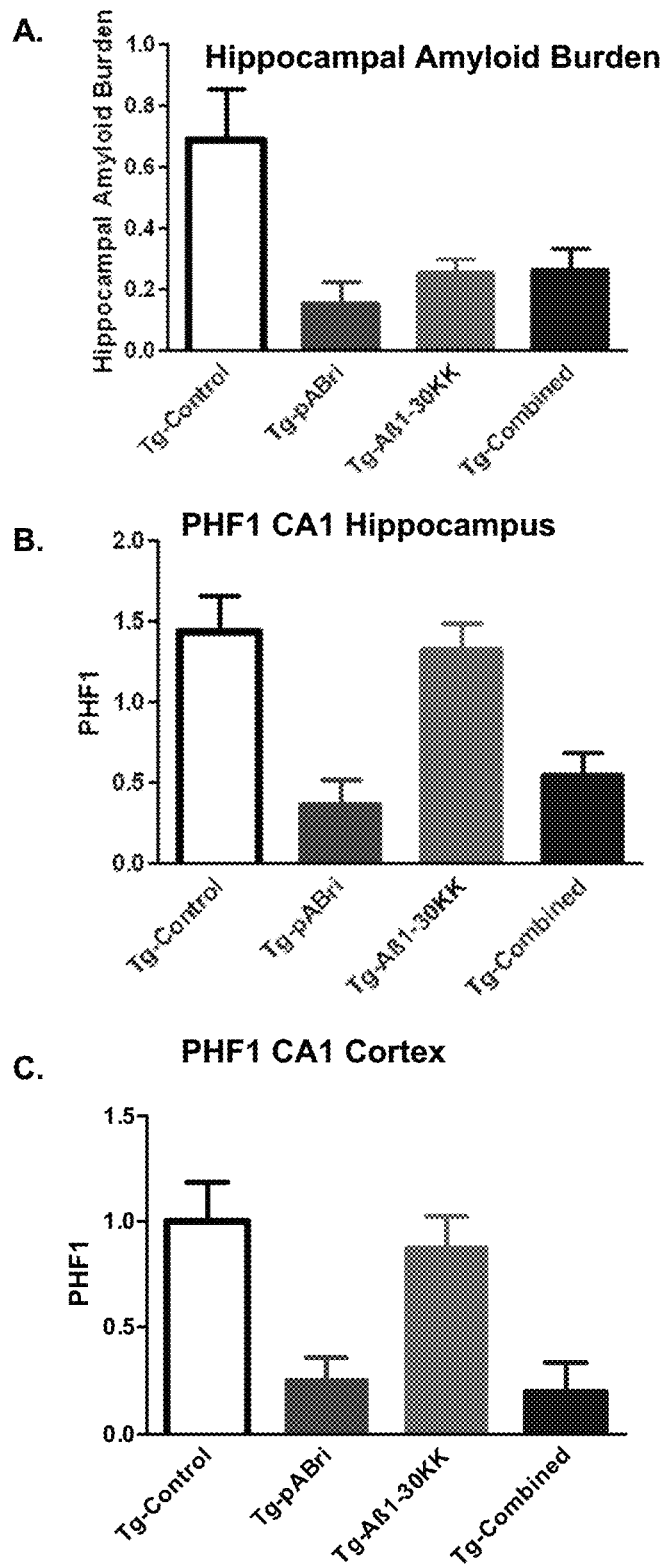
FIGS. 6A-6C depict the amyloid and paired helical fiber (PHF1) burden in Tg3x transgenic control and vaccinated animals.

There was a significant reduction in hippocampal amyloid burden in Tg3x animals administered polymerized ABri (Tg-pABri), polymerized Aβ1-30$_{18}$K$_{19}$K (Tg-AB1-30KK), or the combination of polymerized peptides (Tg-combined) compared to transgenic control (Tg-control) animals as shown in FIG. 6A. There was also a significant reduction in PHF1 in the hippocampus (FIG. 6B) and cortex (FIG. 6C), respectively, of Tg3x animals administered polymerized ABri or the combination of polymerized ABri and Aβ1-30$_{18}$K$_{19}$K. No significant difference in PHF1 burden in the hippocampus or cortex was found between Tg-control and Tg-Aβ1-30$_{18}$K$_{19}$K treated animals.

Figures 7A, 7B:
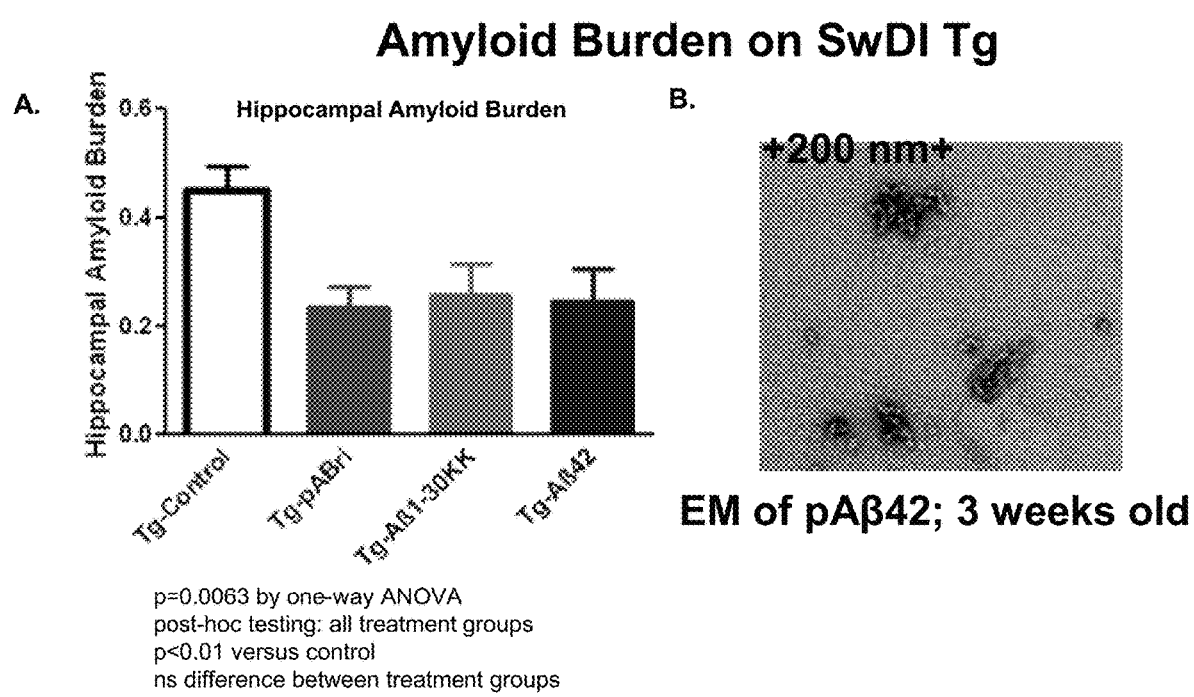
FIGS. 7A-7B depict the amyloid burden in SwDI transgenic control and vaccinated animals.

There was a significant reduction in the hippocampal amyloid burden in SwDI Tg animals vaccinated with polymerized ABri, Aβ1-30K$_{18}$K$_{19}$, or Aβ1-42 compared to control Tg mice (see FIG. 7A).

Example 4—Aβ1-42 Peptide Polymerization and Assessment of Conformation

Figure 8A:
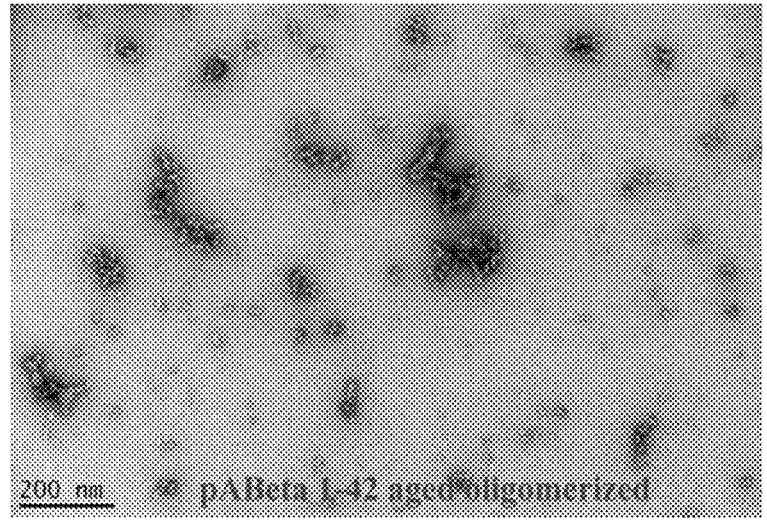
FIGS. 8A-8B are EM images of aged Aβ1-42 peptides.
Figure 8B:
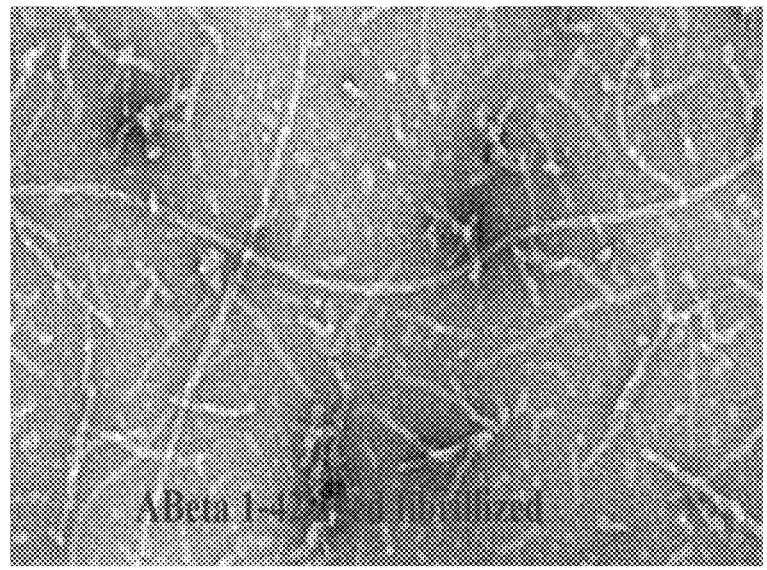

To examine the stability of polymerized peptide conformation over time, aged Aβ1-42 was analyzed by electron microscopy. As shown in the EM photomicrograph of FIG. 7B the polymerized Aβ1-42 peptide is predominately in the form of spherical particles of ~200 nm at 3 weeks post polymerization. Similarly, the EM photomicrograph of FIG. 8A shows that Aβ1-42 peptide aged for 3 months after controlled polymerization with glutaraldehyde maintains the spherical particle form that is typical of oligomerized peptides/proteins without any evidence of fibril formation. In contrast, a non-polymerized Aβ1-42 peptide from the same synthesis batch as the peptide in FIG. 8A shows complete fibrillization at 3 months.

Discussion of Examples 1-4

In summary, controlled polymerized forms of Aβ1-42 and Aβ1-30K$_{18}$K$_{19}$ have been obtained. As demonstrated by EM analysis the Aβ1-42 polymerized form does not produce fibrils when aged. The polymerized peptides are stable immunogens that produce an immune response that more specifically targets the oligomeric pathogenic form of Aβ without targeting the normal, physiological conformers of Aβ. Vaccination of TgSwDI and Tg3x animals with polymerized ABri, Aβ1-42 or Aβ1-30K$_{18}$K$_{19}$ elicits a good antibody response and produces cognitive benefits. Administration of polymerized Aβ1-42 reduces amyloid beta pathology, reduces AB oligomer levels, and diminishes congophilic angiopathy, which is extensive in the SwDI animal model. As demonstrated herein, polymeric synthetic peptides have been designed that mimic the secondary structure found in amyloid and oligomeric forms of AB and pathological forms of tau. The antibody response elicited can target both amyloid and tau pathology resulting in a cognitive benefit, pathology burden reduction, and lack of apparent autoimmune toxicity. Collectively, this data demonstrates these polymeric synthetic peptides are excellent candidates for comprehensive immunomodulation in AD.

Materials and Methods for Example 5

Figure 9:
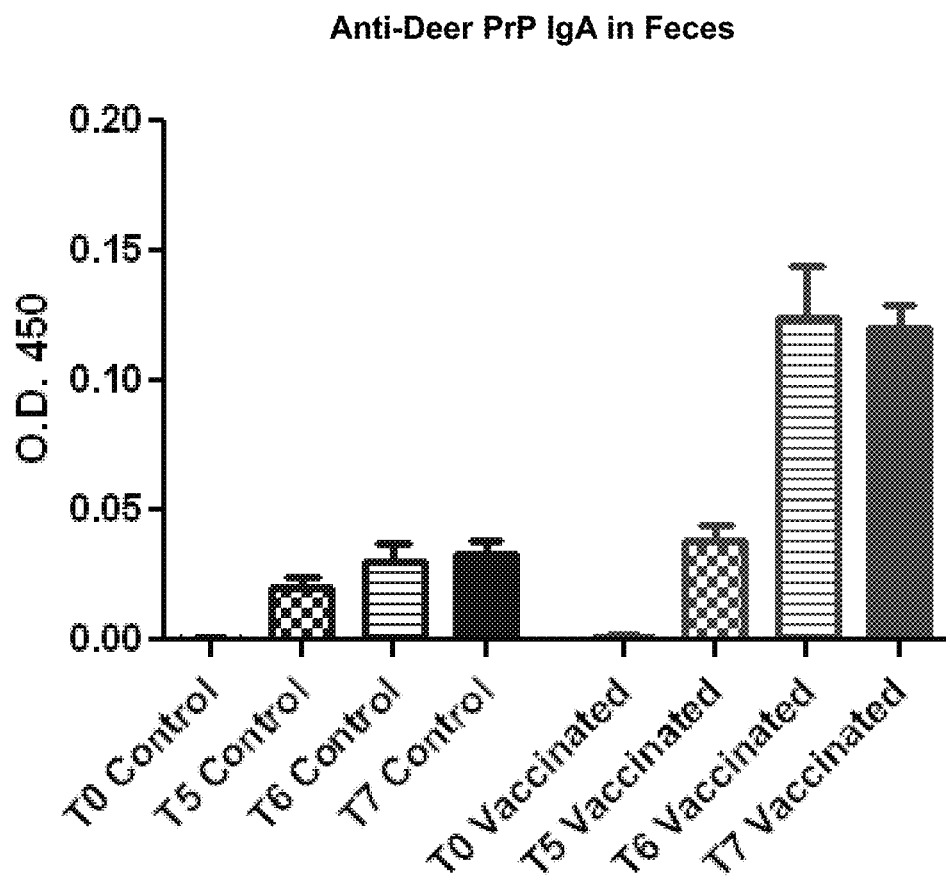
FIG. 9 shows specific anti-PrP IgA antibodies in feces of control and deer vaccinated with prion protein (PrP) as measured by ELISA. White tail deer were orally inoculated with an attenuated *salmonella* carrying deer-PrP or an empty vector (control) four times over a period of a few months following the protocol for mucosal vaccination described in Goni et al., "High Titers of Mucosal and Systemic Anti-PrP Antibodies Abrogate Oral Prion Infection in Mucosal-Vaccinated Mice," *Neurosci.* 153:679-686 (2008), which is hereby incorporated by reference in its entirety. Animals were subsequently orally boosted with a mixture of polymerized PrP and polymerized recombinant PrP peptides as described in the Examples herein. Antibody titers were measure before the first inoculation (T0), after the fourth inoculation (T5), and ten days after the boost (T6). The boost with PrP and polymerized PrP fragments was repeated two months after the first boost, and titers were again measured 10 days after the second boost (T7). The control group did not develop any noticeable titer whereas the vaccinated group showed some increase in mucosa titer after the immune response was established with the *salmonella* oral delivery. The titers were very low (T5) but were greatly enhanced after the animals were boosted with the polymerized PrP and PrP fragments (T6 and T7) showing the importance of these antigenic preparation to have a sustainable immune response.

Five White Tail deer were inoculated (vaccinated group) orally with an attenuated *salmonella* carrying deer PrP to stimulate the mucosal immune system. At the same time six White Tail deer were inoculated with the same strain of attenuated *salmonella* but without any insert or foreign protein to be delivered (Control group). The inoculations were repeated 4 times over a period of a few months following the protocol described by Goni et al., "High Titers of Mucosal and Systemic Anti-PrP Antibodies Abrogate Oral Prion Infection in Mucosal-Vaccinated Mice," *Neurosci.* 153:679-686 (2008), which is hereby incorporated by reference in its entirety.

Before the first inoculation (T0) and after the fourth inoculation (T5) samples of serum, saliva, and feces were taken and the specific antibodies against PrP were measured by ELISA. Subsequently vaccinated animals were orally boosted with a mixture of recombinant polymerized deer PrP protein and polymerized PrP fragments corresponding to amino acid residues 121-166; 13-155; 155-200 and 169-230 of the mouse prion protein of SEQ ID NO: 11 below.

```
  1 manlgywlla lfvtmwtdvg lckkrpkpgg wntggsrypg qgspggnryp pqggtwgqph
 61 gggwgqphgg swgqphggsw gqphgggwgq gggthnqwnk pskpktnlkh vagaaaagav
121 vgglggymlg samsrpmihf gndwedryyr enmyrypnqv yyrpvdqysn qnnfvhdcvn
181 itikqhtvtt ttkgenftet dvkmmervve qmcvtqyqke sqayydgrrs sstvlfsspp
241 villisflif livg
```

The PrP peptides and recombinant protein were subject to controlled polymerization as described herein and Goni et al, "Immunomodulation Targeting Abnormal Protein Conformation Reduces Pathology in a Mouse Model of Alzheimer's Disease," *PLoS One* 5(10):e13391 (2010), which is hereby incorporated by reference in its entirety. The polymerized PrP fragments and PrP protein were dissolved in sterile saline and delivered with 9:1 sodium hydroxide (Alum).

Ten days after delivery of the first booster, serum, saliva, and feces samples were taken (T6). Two months later the same boost with polymerized PrP and polymerized PrP fragments was repeated. Ten days after the second booster, serum, saliva, and feces were collected (T7).

The animals were subsequently boosted again and then orally challenged by delivering Chronic Wasting Disease (CWD) brain homogenate in bait. Samples were taken at different times and survival was assessed to the time the animals showed clear signs of prion disease.

Example 5—Administration of Polymerized PrP Protein/Peptides Protects Against Chronic Wasting Disease in Deer FIGS. 9 and 10 show the anti-PrP IgA antibody titers in feces and anti-PrP IgM antibody titers in plasma, respectively, in both control and vaccinated deer over the course of the treatment regimen described above. The control group did not develop any noticeable IgA titer whereas the vaccinated group showed some increase in mucosa titer after the immune response was established with the *salmonella* oral delivery. The IgA titers were initially very low (T5) but were greatly enhanced after the animals were boosted with the polymerized PrP and PrP fragments (T6 and T7) showing the importance of these antigenic preparation on generating a sustainable immune response (FIG. 9). With regard to IgM antibody titers, the control group did not show any noticeable increase in antibody titer; whereas the vaccinated group showed some concomitant IgM titer in serum at the same time of the mucosal response (T5). Anti-PrP antibody titers in the vaccinated animals greatly increased after the two boosts with the polymerized PrP and PrP fragments showing that this type of boost could invoke a therapeutic serum response.

Figure 10:
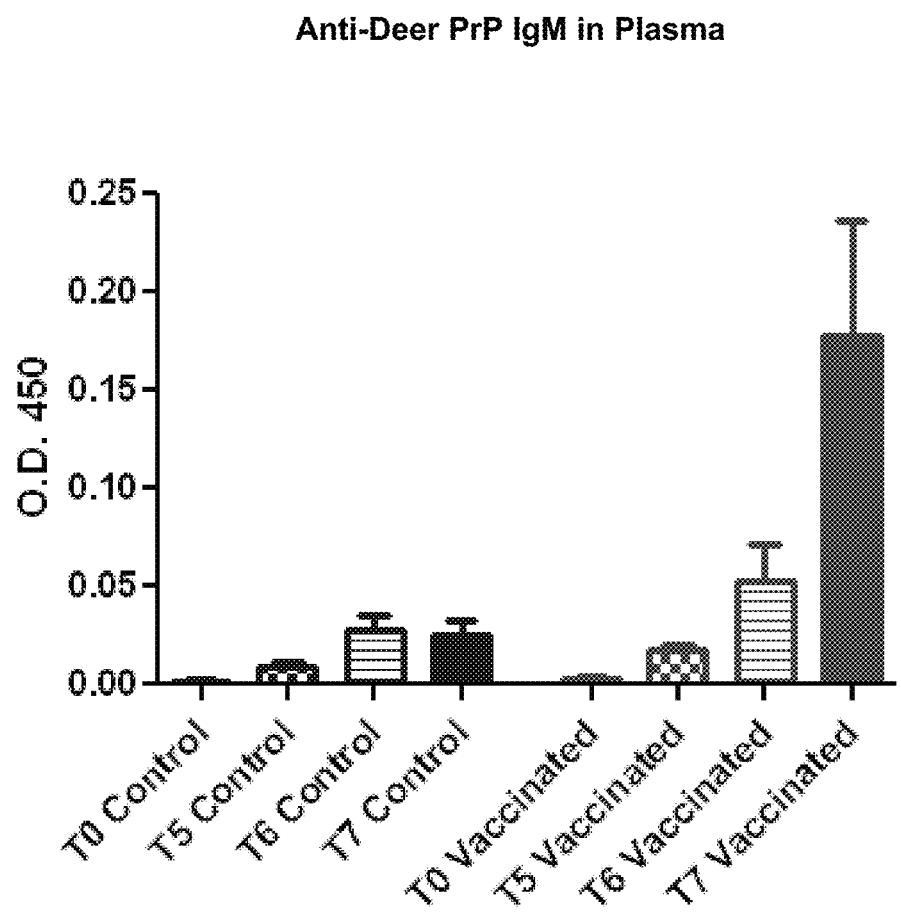
FIG. 10 shows serum anti-PrP IgM antibodies of control deer and deer vaccinated with PrP as described in FIG. 9. Again the control group did not show any noticeable increase in antibody titer; whereas the vaccinated group showed some concomitant IgM titer in serum at the same time of the mucosal response (T5). Anti-PrP antibody titers in the vaccinated animals greatly increased after the two boosts with the polymerized PrP and PrP fragments showing that this type of boost could invoke a therapeutic serum response. Vaccinated vs. control at T0 not significant, * p<0.05,  p=0.0009, * p<0.0001 (two-tailed test).
Figure 11:
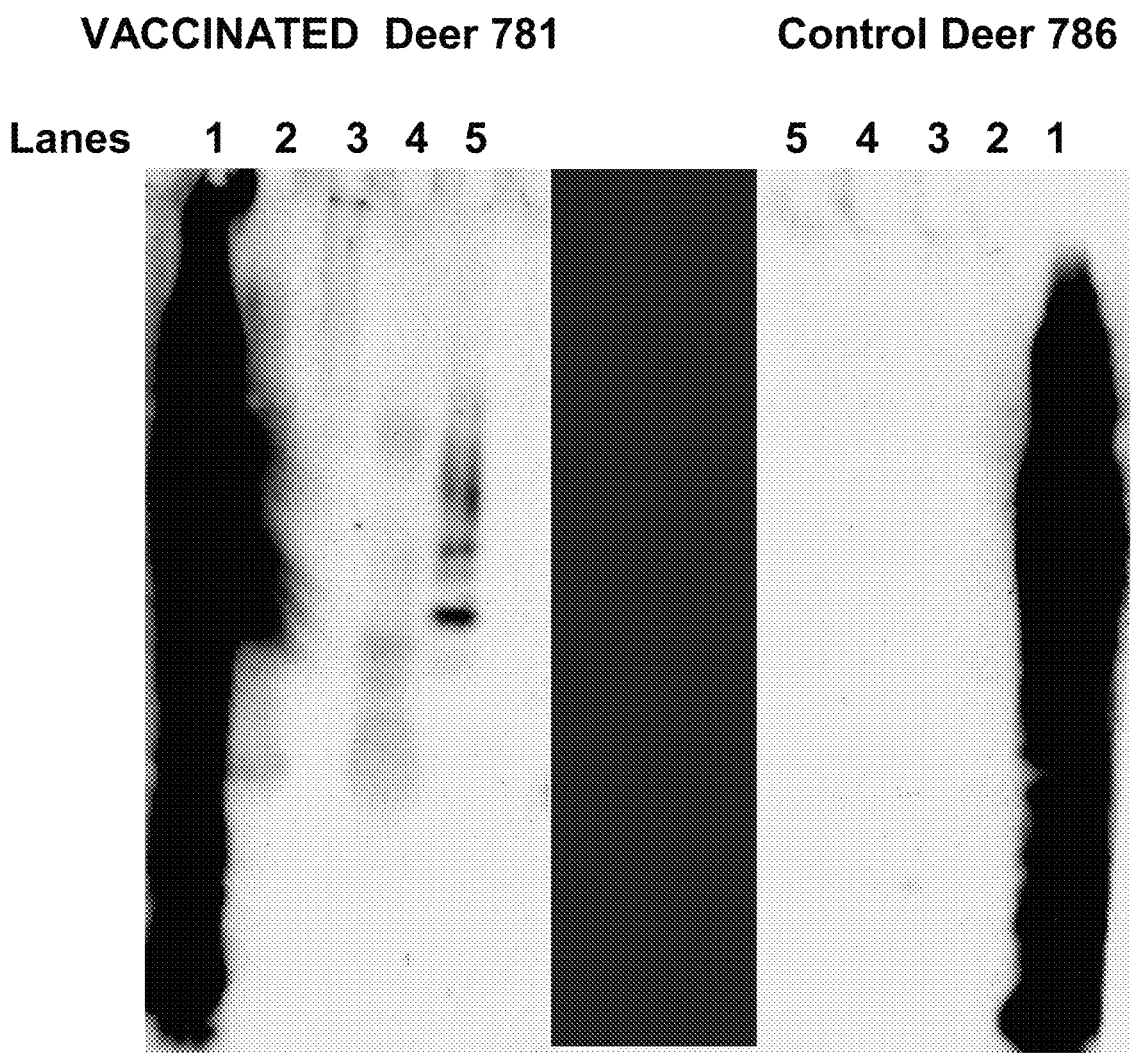
FIG. 11 shows immunoblots of *salmonella* lysate (lane 1), sheep PrP (lane 2), polymerized sheep PrP (lane 3), deer PrP (lane 4), and polymerized deer PrP (lane 5) that were developed using purified antibodies from vaccinated animal 781 at T7 and control animal 786 at T7. Both animals mounted a good immune response to *salmonella* (lane 1); however, only the vaccinated animal had antibodies against different deer PrP molecules (lane 4) and the oligomers present in the polymerized deer PrP (lane 5). Vaccinated vs. control at T0 not significant, * p<0.017,  p=0.0022, * p<0.01 (two-tailed test).

An analysis of the antibody specificity in the vaccinated deer found that the antibodies produced are specific to prion protein. FIG. 10 contains immunoblot data using purified antibodies from T7 in vaccinated animal 781 and control animal 786. Lane 1 of the blot contains *salmonella* lysate, to which antibodies in both animals were highly reactive to. Lanes 4 and 5 contain deer PrP and polymerized deer PrP. The bands appearing in both lanes of the blot incubated with antibodies from the vaccinated animal but not in the lanes of the blot incubated with antibodies from the control animal indicate the generation and presence of deer PrP antibodies in the vaccinated, but not control animals. Lanes 2 and 3 contain sheep PrP and polymerized sheep PrP. The absence of bands in these lanes indicates the specificity of the antibody response observed in the vaccinated animals, i.e., the generated antibodies are specific for deer PrP.

Figure 12:
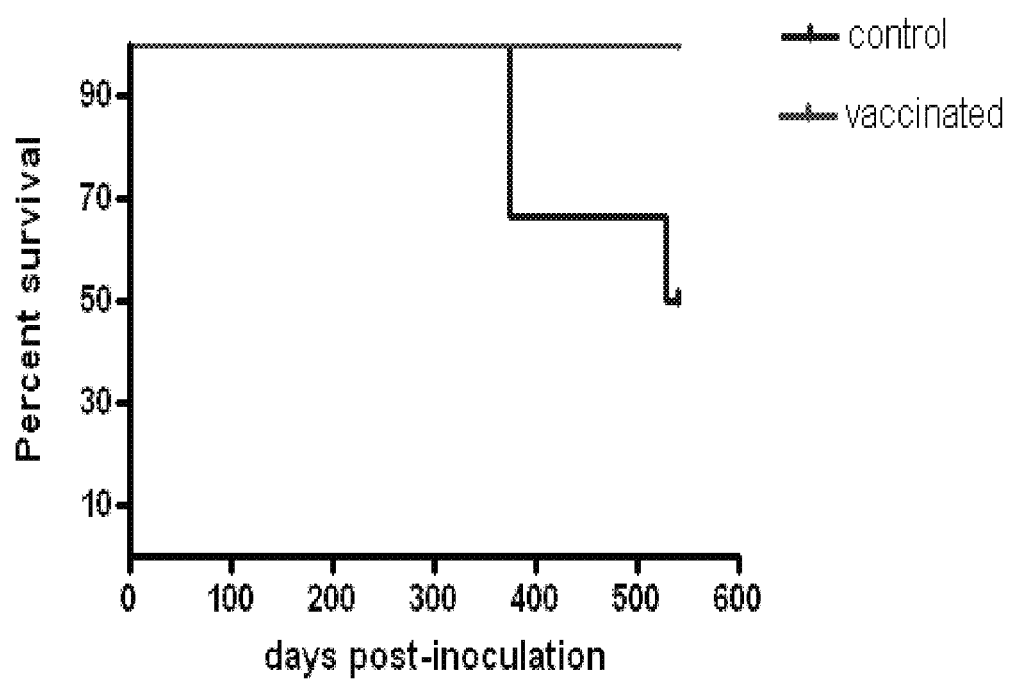
FIG. 12 is a Kaplan and Meier survival curve showing the protective effect of PrP vaccination in White Tail Deer at 18 months after challenge. Three out of six control animals became sick with the prionoses Chronic Wasting Disease and were properly euthanized. None of the vaccinated animals had signs of the disease at 18-months. Protection for the progression of the disease is evident and due to the immune response elicited by the inoculations involving the polymerized PrP and PrP fragments.

PrP vaccination was clearly protective as indicated by the Kaplan Meier survival curve of FIG. 12. Both vaccinated and control animals were challenged with exposure to CWD. Three out of the six control animals became with sick prionoses CWD and had to be properly euthanized. In contrast, none of the vaccinated animals had any signs of disease over the course of 18 months after challenge.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A non-amyloidogenic and non-fibrillogenic heteropolymer product formed from two or more different protein and/or peptide monomers, wherein each protein and/or peptide monomer forming said product is covalently linked to one or more other protein and/or peptide monomers forming said product by one or more glutaraldehyde molecules, and wherein each of the two or more different protein and/or peptide monomers is independently selected from the group consisting of amyloid-beta (Aβ) peptide, an u-synuclein protein or peptide, a tau protein or peptide, a TAR DNA-binding protein 43 (TDP-43) protein or peptide, an amylin protein or peptide, and a priori protein (PrP) protein or peptide.

2. The heteropolymer product of claim 1, wherein one of the two or more different protein and/or peptide monomers is an A13 peptide comprising the amino acid sequence selected from the group consisting of amino acid residues 1-16 of SEQ ID NO:1, amino acid residues 1-20 of SEQ ID NO: 1, amino acid residues 1-30 of SEQ ID NO:1, amino acid residues 1-40 of SEQ ID NO:1, amino acid residues 1-42 of SEQ ID NO:1, amino acid residues 10-30 of SEQ NO:1, amino acid residues 20-40 of SEQ ID NO:1, and amino acid residues 20-42 of SEQ ID NO:1.

3. The heteropolymer product of claim 2, wherein the A13 peptide comprises amino acid residues 1-42 of SEQ ID NO:1.

4. The heteropolymer product of claim 1, wherein one of the two or more different protein and/or peptide monomers is an Aβ peptide comprising the amino acid sequence selected from the group consisting of amino acid residues 1-30 of SEQ ID NO:2 (Aβ1-30$K_{18}K_{19}$), amino acid residues 1-40 of SEQ NO:2 (Aβ1-40$K_{18}K_{19}$), amino acid residues 1-42 of SEQ ID N0:2 (Aβ1-42$K_{18}K_{19}$), amino acid residues 1-20 of SEQ ID NO:2 (Aβ1-20$K_{18}K_{19}$), amino acid residues 10-30 of SEQ ID NO:2 (Aβ10-30$K_{18}K_{19}$), amino acid residues 10-40 of SEQ ID NO:2 (Aβ10-40$K_{18}1_{(19)}$), amino acid residues 10-42 of SEQ ID NO:2 (Aβ10-40$K_{18}K_{19}$), amino acid residues 20-40 of SEQ ID NO:2 (Aβ20-40$K_{18}K_{19}$), and amino acid residues 20-42 of SEQ ID NO:2 (Aβ20-42$K_{18}K_{19}$).

5. The heteropolymer product of claim 4, wherein the Aja peptide comprises amino acid residues 1-30 of SEQ ID NO:2 (Aβ1-30$K_{18}K_{19}$.

6. The heteropolymer product of claim 1, wherein one of the two or more different protein and/or peptide monomers is an α-synuclein protein comprising the amino acid sequence of SEQ NO:3, or a peptide derived from the amino acid sequence of SEQ NO:3, said peptide comprising at least 10 contiguous amino acid residues and having at least 80% homology to the amino acid sequence of SEQ ID NO: 3.

7. The heteropolymer product of claim 1, wherein one of the two or more different protein and/or peptide monomers is a mu protein comprising the amino acid sequence of SEQ ID NO: 4, or a peptide derived from the amino acid sequence of SEQ ID NO:4, said peptide comprising at least 10 contiguous amino acid residues and having at least 80% homology to the amino acid sequence of SEQ ID NO: 4.

8. The heteropolymer product of claim 1, wherein one of the two or more different protein and/or peptide monomers is a TDP-43 protein comprising the amino acid sequence of SEQ ID NO: 5, or a peptide derived from the amino acid sequence of SEQ ID NO: 5, said peptide comprising at least 10 contiguous amino acid residues and having at least 80% homology to the amino acid sequence of SEQ ID NO: 5.

9. The heteropolymer product of claim 1, wherein one of the two or more different protein and/or peptide monomers is an amylin protein comprising the amino acid sequence of SEQ ID NO:6, or a peptide derived from the amino acid sequence of SEQ ID NO:6, said peptide comprising at least 10 contiguous amino acid residues and having at least 80% homology to the amino acid sequence of SEQ ID NO: 6.

10. The heteropolymer product of claim 1, wherein one of the two or more different protein and/or peptide monomers is a PrP protein or peptide comprising the amino acid sequence of SEQ ID NO:7, or a peptide derived thereof, said peptide comprising at least 10 contiguous amino acid residues and having at least 80% homology to the amino acid sequence of SEQ ID NO:7.

11. The heteropolymer product of claim 1, wherein the heteropolymer product comprises one or more amyloid-beta (Aβ) peptides covalently linked to one or more α-synuclein proteins or peptides.

12. The heteropolymer product of claim 1, wherein the heteropolymer product comprises one or more amyloid-beta (Aβ) peptides covalently linked to one or more tau peptides.

13. The heteropolymer product of claim 1, wherein the heteropolymer product comprises one or more TDP-43 peptides covalently linked to one or more amyloid-beta (Aβ) peptides and/or one or more tau peptides.

14. The heteropolymer product of claim 1, wherein said product is non-amyloidogenic and non-fibrillogenic.

15. The heteropolymer product of claim 1, wherein an adjuvant polypeptide is linked in frame to one or more of the protein and/or peptide monomers of the heteropolymer product.

16. The heteropolymer product of claim 15, wherein the adjuvant polypeptide is selected from the group consisting of cholera, toxin B, flagellin, human papillomavirus L1 or L2 protein, herpes simplex glycoprotein D (gD), complement C4 binding protein, TL4 ligand, and IL-1β.

17. The heteropolymer product of claim 15, wherein the one or more protein and/or peptide monomers of the heteropolymer product further comprise a linker sequence connecting the protein or peptide monomer and the adjuvant polypeptide.

18. The heteropolymer product of claim 1, wherein an immunogenic carrier molecule is conjugated to one or more of the protein and/or peptide monomers of the heteropolymer product.

19. The heteropolymer product of claim 18, wherein the immunogenic carrier molecule is covalently or non-covalently bonded to the one or more protein and/or peptide monomers of the heteropolymer product.

20. The heteropolymer product of claim 18, wherein the immunogenic carrier molecule is selected from the group consisting of bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

21. A pharmaceutical composition comprising:
the heteropolymer product of claim 1 and
a pharmaceutically acceptable carrier.

22. The pharmaceutical composition of claim 21 further comprising:
an adjuvant.

23. A non-amyloidogenic and non-fibrillogenic heteropolymer product formed from two or more different protein and/or peptide monomers, Wherein each protein and/or peptide monomer forming said product is covalently linked by a controlled glutaraldehyde reaction to one or more other protein and/or peptide monomers forming said product, and wherein each of the two or more different protein and/or peptide monomers is independently selected from the group consisting of an amyloid-beta (Aβ) peptide, an α-synuclein protein or peptide, a tau protein or peptide, a TAR DNA-binding protein 43 (TDP-43) protein or peptide, an amylin protein or peptide, and a prion protein (PrP) protein or peptide.

* * * * *

UNITED STATES PATENT AND TRADEMARK OFFICE
CERTIFICATE OF CORRECTION

PATENT NO. : 11,332,506 B2
APPLICATION NO. : 15/933146
DATED : May 17, 2022
INVENTOR(S) : Wisniewski and Goni It is certified that error appears in the above-identified patent and that said Letters Patent is hereby corrected as shown below:

In the Claims

In Claim 1 at Column 45, Line 33, delete "u-synuclein" and insert --α-synuclein--; and
At Column 45, Line 36, delete "priori" and insert --prion--.

In Claim 2 at Column 45, Line 40, delete "A13" and insert --Aβ--.

In Claim 3 at Column 45, Line 48, delete "A13" and insert --Aβ--.

In Claim 4 at Column 45, Line 57, delete "N0:" and insert --NO:--.

In Claim 5 at Column 45, Line 65, delete "Aja" and insert --Aβ--; and
At Column 45, Line 67, insert --)-- before the period.

In Claim 7 at Column 46, Line 33, delete "mu" and insert --tau--.

In Claim 23 at Column 48, Line 16, delete "Wherein" and insert --wherein--.

Signed and Sealed this
Nineteenth Day of September, 2023

*Katherine Kelly Vidal*

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 42
<212> TYPE: PRT
<213> ORGANISM: Artificial
<220> FEATURE:
<223> OTHER INFORMATION: A-beta peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 42
<212> TYPE: PRT
<213> ORGANISM: Artificial
<220> FEATURE:
<223> OTHER INFORMATION: A-beta peptide

<400> SEQUENCE: 2

Asp Ala Glu Phe Arg His Asp Ser Gly Tyr Glu Val His His Gln Lys
1               5                   10                  15

Leu Lys Lys Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 140
<212> TYPE: PRT
<213> ORGANISM: Homo sapiens

<400> SEQUENCE: 3

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 441
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val 245                 250                 255
Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                        405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 5
<211> LENGTH: 414
<212> TYPE: PRT
<213> ORGANISM: Homo sapiens

<400> SEQUENCE: 5

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
            115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

```
Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 6
<211> LENGTH: 62
<212> TYPE: PRT
<213> ORGANISM: Homo sapiens

<400> SEQUENCE: 6

His Gln Val Glu Lys Arg Lys Cys Asn Thr Ala Thr Cys Ala Thr Gln
1               5                   10                  15

Arg Leu Ala Asn Phe Leu Val His Ser Ser Asn Asn Phe Gly Ala Ile
            20                  25                  30

Leu Ser Ser Thr Asn Val Gly Ser Asn Thr Tyr Gly Lys Arg Asn Ala
        35                  40                  45

Val Glu Val Leu Lys Arg Glu Pro Leu Asn Tyr Leu Pro Leu
    50                  55                  60

<210> SEQ ID NO 7
<211> LENGTH: 253
<212> TYPE: PRT
<213> ORGANISM: Homo sapiens

<400> SEQUENCE: 7

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30
```

```
Thr Gly Gly Ser Arg Tyr Pro Gly Gln Gly Ser Pro Gly Gly Asn Arg
            35                  40                  45

Tyr Pro Pro Gln Gly Gly Gly Trp Gly Pro His Gly Gly
        50                  55                  60

Trp Gly Gln Pro His Gly Gly Trp Gly Pro His Gly Gly
65                  70                  75                  80

Trp Gly Gln Pro His Gly Gly Trp Gly Gln Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
            115                 120                 125

Val Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
            195                 200                 205

Val Val Glu Gln Met Cys Ile Thr Gln Tyr Glu Arg Glu Ser Gln Ala
            210                 215                 220

Tyr Tyr Lys Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 8
<211> LENGTH: 13
<212> TYPE: PRT
<213> ORGANISM: Artificial
<220> FEATURE:
<223> OTHER INFORMATION: ABri peptide

<400> SEQUENCE: 8

Cys Ser Arg Thr Val Lys Lys Asn Ile Ile Glu Glu Asn
1               5                   10

<210> SEQ ID NO 9
<211> LENGTH: 13
<212> TYPE: PRT
<213> ORGANISM: Artificial
<220> FEATURE:
<223> OTHER INFORMATION: ADan peptide

<400> SEQUENCE: 9

Cys Phe Asn Leu Phe Leu Asn Ser Gln Glu Lys His Tyr
1               5                   10

<210> SEQ ID NO 10
<211> LENGTH: 31
<212> TYPE: PRT
<213> ORGANISM: Artificial
<220> FEATURE:
<223> OTHER INFORMATION: ABri/ADan fusion peptide

<400> SEQUENCE: 10

Cys Ser Arg Thr Val Lys Lys Asn Ile Ile Glu Glu Asn Gly Ser Gly
```

```
                1               5                  10                 15
            Ser Gly Cys Phe Asn Leu Phe Leu Asn Ser Gln Glu Lys His Tyr
                        20                 25                 30

<210> SEQ ID NO 11
<211> LENGTH: 254
<212> TYPE: PRT
<213> ORGANISM: Mouse

<400> SEQUENCE: 11

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Trp Gly Gln Gly Gly Thr His Asn
                85                  90                  95

Gln Trp Asn Lys Pro Ser Lys Pro Lys Thr Asn Leu Lys His Val Ala
                100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 12
<211> LENGTH: 30
<212> TYPE: PRT
<213> ORGANISM: Artificial
<220> FEATURE:
<223> OTHER INFORMATION: A-beta1-30k18k19

<400> SEQUENCE: 12

Asp Ala Glu Phe Arg His Asp Ser Gly Tyr Glu Val His His Gln Lys
1               5                   10                  15

Leu Lys Lys Phe Ala Glu Asp Val Gly Ser Asn Lys Gly Ala
            20                  25                  30

<210> SEQ ID NO 13
```

```
<211> LENGTH: 4
<212> TYPE: PRT
<213> ORGANISM: Artificial
<220> FEATURE:
<223> OTHER INFORMATION: Glycine-rich linker

<400> SEQUENCE: 13

Gly Ser Gly Ser
1

<210> SEQ ID NO 14
<211> LENGTH: 5
<212> TYPE: PRT
<213> ORGANISM: Artificial
<220> FEATURE:
<223> OTHER INFORMATION: Glycine-rich linker

<400> SEQUENCE: 14

Gly Ser Gly Ser Gly
1               5
```